(12) United States Patent
Giftakis et al.

(10) Patent No.: US 7,809,443 B2
(45) Date of Patent: Oct. 5, 2010

(54) ELECTRICAL STIMULATION TO ALLEVIATE CHRONIC PELVIC PAIN

(75) Inventors: Jonathon E. Giftakis, Maple Grove, MN (US); Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 516 days.

(21) Appl. No.: 11/413,621

(22) Filed: Apr. 28, 2006

(65) Prior Publication Data

US 2007/0179559 A1  Aug. 2, 2007

Related U.S. Application Data

(63) Continuation-in-part of application No. 11/344,580, filed on Jan. 31, 2006, now abandoned.

(51) Int. Cl.
*A61N 1/34* (2006.01)
(52) U.S. Cl. .......................... 607/46; 607/39
(58) Field of Classification Search .................. 607/39, 607/45; 600/347
See application file for complete search history.

(56) References Cited

U.S. PATENT DOCUMENTS

| | | | |
|---|---|---|---|
| 5,501,703 A | | 3/1996 | Holsheimer et al. |
| 5,634,462 A | * | 6/1997 | Tyler et al. .................. 600/377 |
| 5,660,854 A | | 8/1997 | Haynes et al. |
| 5,792,187 A | | 8/1998 | Adams |
| 6,169,924 B1 | | 1/2001 | Meloy et al. |
| 6,862,479 B1 | | 3/2005 | Whitehurst et al. |
| 6,885,895 B1 | | 4/2005 | Whitehurst et al. |
| 6,944,497 B2 | | 9/2005 | Stypulkowski |
| 7,292,890 B2 | * | 11/2007 | Whitehurst et al. ........... 607/45 |
| 2002/0055761 A1 | | 5/2002 | Mann et al. |
| 2003/0100930 A1 | | 5/2003 | Cohen et al. |
| 2003/0236557 A1 | | 12/2003 | Whitehurst et al. |
| 2004/0073197 A1 | | 4/2004 | Kim |
| 2004/0122477 A1 | | 6/2004 | Whitehurst et al. |
| 2005/0033372 A1 | | 2/2005 | Gerber |

(Continued)

OTHER PUBLICATIONS

Murovic, J. A., Kim, D. H., Tiel, R. L., Kline, D. G., "Surgical Management of 10 Genitofemoral Neuralgias at the Louisiana State University Health Sciences Center," Neurosurgery, vol. 56, No. 2, pp. 298-303, www.neurosurgery-online.com, Feb. 2005.

(Continued)

*Primary Examiner*—Carl H Layno
*Assistant Examiner*—Brian T Gedeon
(74) *Attorney, Agent, or Firm*—Shumaker & Sieffert, P.A.

(57) ABSTRACT

The disclosure describes a method and system for applying electrical stimulation to a genitofemoral nerve or a genital branch of a genitofemoral nerve of a patient. The system includes electrical stimulators that apply electrical stimulation for alleviation of pelvic pain. The system may apply electrical stimulation for pelvic pain in men or women. The electrical stimulators may comprise various types of electrodes such as cuff electrodes, electrode leads, and microstimulators implanted at various locations proximate to a single or both genitofemoral nerves and the genital branch of a single or both genitofemoral nerves of a patient. When implanted proximate to a genital nerve branch, the electrode may be implanted proximate to the genital nerve branch. In a male patient stimulation may be delivered proximate to the spermatic cord, which contains a portion of the genital nerve branch.

26 Claims, 14 Drawing Sheets

U.S. PATENT DOCUMENTS

| | | | |
|---|---|---|---|
| 2005/0033373 | A1 | 2/2005 | Gerber |
| 2005/0085486 | A1 | 4/2005 | Gonzalez-Cadavid et al. |
| 2005/0096709 | A1 | 5/2005 | Skwarek et al. |
| 2005/0113877 | A1 | 5/2005 | Spinelli et al. |
| 2005/0113878 | A1 | 5/2005 | Gerber |
| 2005/0131484 | A1 | 6/2005 | Boveja et al. |
| 2005/0143789 | A1 | 6/2005 | Whitehurst et al. |
| 2005/0216069 | A1 | 9/2005 | Cohen et al. |
| 2005/0222628 | A1 | 10/2005 | Krakousky |
| 2005/0228451 | A1 | 10/2005 | Jaax et al. |
| 2006/0004421 | A1* | 1/2006 | Bennett et al. ............... 607/41 |
| 2006/0004429 | A1* | 1/2006 | Mrva et al. ................. 607/116 |
| 2006/0020297 | A1 | 1/2006 | Gerber et al. |
| 2006/0069414 | A1* | 3/2006 | Imran et al. .................. 607/40 |
| 2006/0095088 | A1 | 5/2006 | De Ridder |
| 2006/0129028 | A1* | 6/2006 | Krakousky ................... 600/40 |
| 2006/0149345 | A1 | 7/2006 | Boggs, II et al. |
| 2006/0155344 | A1 | 7/2006 | Rezai et al. |
| 2007/0021801 | A1 | 1/2007 | Heruth et al. |
| 2007/0021802 | A1 | 1/2007 | Heruth et al. |
| 2007/0039625 | A1 | 2/2007 | Heruth et al. |
| 2007/0173900 | A1 | 7/2007 | Siegel et al. |

OTHER PUBLICATIONS

Kim, D. H., Murovic, J. A., Tiel, R. L., Kline, D. G., "Surgical Management of 33 Ilioinguinal and Iliohypogastric Neuralgias at the Louisiana State University Health Sciences Center," Neurosurgery, vol. 56, No. 5, pp. 1013-1020,, www.neurosurgery-online.com, May, 2005.

Brindley, G. S., "Sacral root and hypogastric plexus stimulators and what these models tell us about autonomic actions on the bladder and urethra," Clinical Science, vol. 70 (Suppl. 14), pp. 41s-44s, 1985.

Granitsiotis, P., Kirk, D.; "Chronic Testicular Pain: An Overview," European Urology, vol. 45, pp. 430-436, 2004.

Sasaoka, N., Kawaguchi, M., Yoshitani, K., Kato, H., Suzuki, A., Furuya, H., "Evaluation of genitofemoral nerve block, in addition to ilioinguinal and iliohypogastric nerve block, duting inguinal hernia repair in children", British Journal of Anaesthesia, vol. 94 No. 2, pp. 243-246, 2005.

Berman, J., Berman, L. "Female Sexual Function and Dysfunction", Annual Meeting of American Urological Association, Inc., May 29, 2002.

Yucel, S., Baskin, L. S., The neuroanatomy of the human scrotum:surgical ramifications:, BJU International, vol. 51, pp. 393-397, 2003.

Levine, L. A., Matkov, T. G., Microsurgical Denervation of the Spermatic Cord as Primary Surgical Treatment of Chronic Orchialgia, The Journal of Urology, vol. 165, pp. 1927-1929, Jun. 2001.

Gillitzer, R., Hampel, C., Wiesner, C., Pahernik, S., Melchior, S., Thuroff, J. W., "Pudendal Nerve Branch Injury During Radical Perineal Prostatectomy," Journal of Urololgy, vol. 67, No. 2, 2006.

Uchio, E. M., Yang, C. C., Kromm, B. G., Bradley, W. E., "Cortical Evoked Responses from the Perineal Nerve," The Journal of Urology, vol. 162, pp. 1983-1986, Dec. 1999.

The Pain Clinic, "Peripheral Nerve Blocks", http://www.painclinic.org/treatment-peripheralnerveblocks.htm, 2006, (10 pages).

Mayo Foundation for Medical Education and Research, "Urinary Incontinence", http://www.mayoclinic.com/health/urinaryincontinence/DS00404/DSECTION=8, 2006, (5 pages).

Mayo Foundation for Medical Education and Research, "Erectile Dysfunction", http://www.mayoclinic.com/health/erectiledysfunction/DS00162/DSECTION=7, Jan. 18, 2006, (3 pages).

New York School of Regional Anesthesia, "Genitofemoral Block", http://www.nysora.com/techniques/genitofemoral_block/, 2006, (3 pages).

Hruby et al., "Anatomy of pudendal nerve at urogenital diaphragm-new critical site for nerve entrapment", Journal of Urology, vol. 66, Issue 5, Nov. 2005, pp. 949-952.

Bolandart et al., European Society of Regional Anaesthesia and Pain Therapy, "Ilioinguinal-Iliohypogastric Block—Single Shot", 2006, (2 pages).

U.S. Appl. No. 11/413,617, filed Apr. 28, 2006 entitled: "Drug Delivery to Alleviate Chronic Pelvic Pain".

U.S. Appl. No. 11/414,505, filed Apr. 28, 2006 entitled: "Drug Delivery to Iliohypogastric Nerve to Alleviate Chronic Pelvic Pain".

U.S. Appl. No. 11/344,580, filed Jan. 31, 2006 entitled: "Electrical Stimulation to Alleviate Chronic Pelvic Pain".

U.S. Appl. No. 11/414,615, filed Apr. 28, 2006 entitled: "Electrical Stimulation of Ilioinguinal Nerve to Alleviate Chronic Pelvic Pain".

U.S. Appl. No. 11/414,614, filed Apr. 28, 2006 entitled: "Electrical Stimulation of Iliohypogastric Nerve to Alleviate Chronic Pelvic Pain".

U.S. Appl. No. 11/414,705, filed Apr. 28, 2006 entitled: "Drug Delivery to Ilioinguinal Nerve to Alleviate Chronic Pelvic Pain".

U.S. Appl. No. 11/414,509, filed Apr. 28, 2006 entitled: "Neuromodulation Therapy for Perineal or Dorsal Branch of Pudendal Nerve".

Responsive Amendment dated Dec. 17, 2008 for U.S. Appl. No. 11/414,614 (11 pgs.).

Office Action dated Jun. 27, 2008 for U.S. Appl. No. 11/414,615 (20 pgs.).

Responsive Amendment dated Sep. 29, 2008 for U.S. Appl. No. 11/414,615 (15 pgs.).

Office Action dated Jun. 30, 2008 for U.S. Appl. No. 11/414,705 (17 pgs.).

Responsive Amendment dated Sep. 29, 2008 for U.S. Appl. No. 11/414,705 (15 pgs.).

Office Action dated Sep. 17, 2008 for U.S. Appl. No. 11/414,614 (6 pgs.).

Lamer et al., "Treatment of Iliohypogastric Neuralgia with Subcutaneous Peripheral Nerve Stimulation," Poster Abstract Form, 9th Annual Meeting, North American Neuromodulation Society, Nov. 10-12, 2005 (1 pg.).

Office Action dated Jul. 20, 2009 for U.S. Appl. No. 11/414,615 (8 pgs.).

Response dated Oct. 20, 2009 for U.S. Appl. No. 11/414,615 (9 pgs.).

Office Action dated Nov. 3, 2009 for U.S. Appl. No. 11/414,614 (10 pgs.).

Responsive Amendment dated Dec. 30, 2009 for U.S. Appl. No. 11/414,614 (16 pgs.).

Office Action dated Jan. 9, 2009 for U.S. Appl. No. 11/414,615 (12 pgs.).

Office Action dated Feb. 26, 2009 for U.S. Appl. No. 11/414,705 (9 pgs.).

Office Action dated Feb. 27, 2009 for U.S. Appl. No. 11/414,614 (10 pgs.).

Request for Continued Examination (RCE) and Responsive Amendment dated May 11, 2009 for U.S. Appl. No. 11/414,615 (11 pgs.).

Request for Continued Examination (RCE) and Responsive Amendment dated May 26, 2009 for U.S. Appl. No. 11/414,705 (10 pgs.).

Request for Continued Examination (RCE) and Responsive Amendment dated May 27, 2009 for U.S. Appl. No. 11/414,614 (9 pgs.).

Office Action dated Mar. 12, 2010 for U.S. Appl. No. 11/414,615 (9 pgs.).

Request for Continued Examination and Responsive Amendment dated Jun. 8, 2010 for U.S. Appl. No. 11/414,615 (15 pgs.).

* cited by examiner

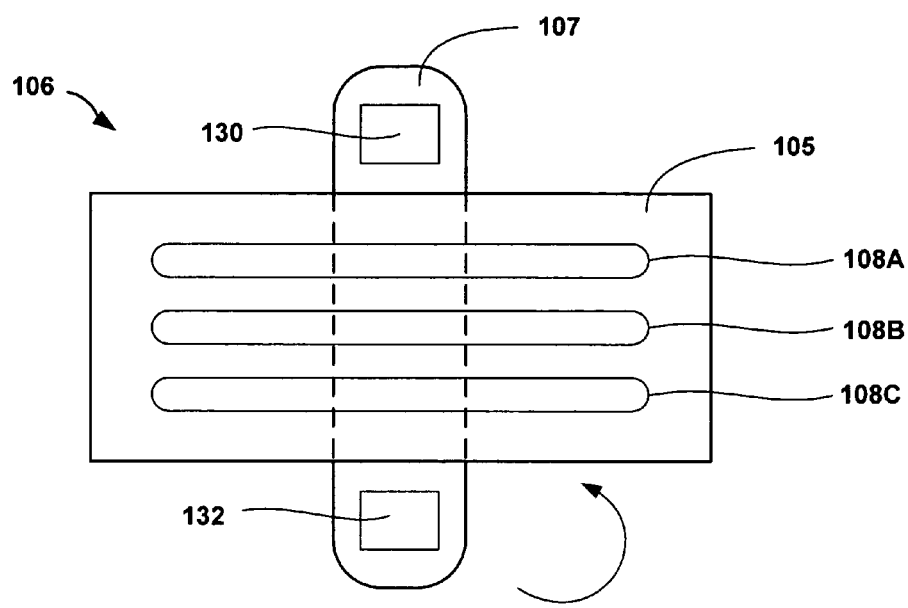
FIG. 11A
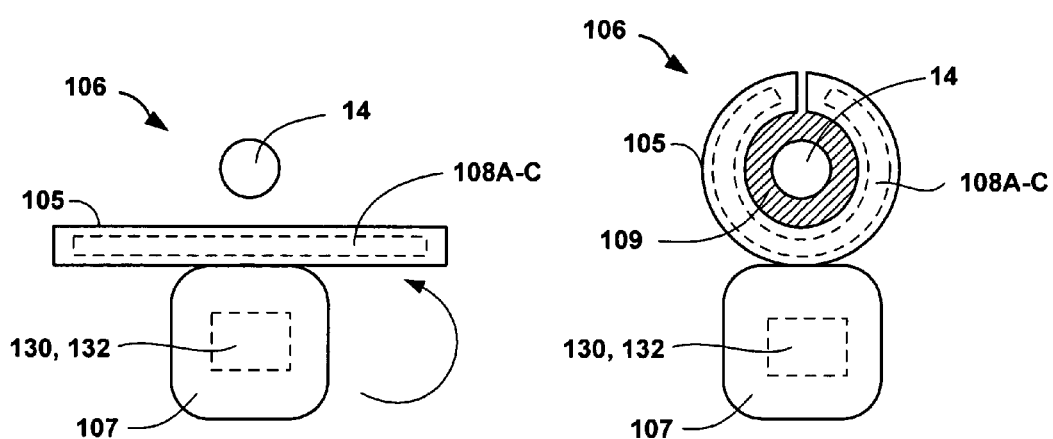
FIG. 11B  FIG. 11C

ELECTRICAL STIMULATION TO ALLEVIATE CHRONIC PELVIC PAIN

This application is a continuation-in-part (CIP) of U.S. application Ser. No. 11/344,580, filed Jan. 31, 2006, the entire content of which is incorporated in this disclosure by reference.

TECHNICAL FIELD

The invention relates to medical devices and, more particularly, to devices for delivering neurostimulation therapy.

BACKGROUND

Pain in the pelvic region, including urogenital pain, may be caused by a variety of injuries or disorders in men and women. For example, chronic testicular pain (CTP), post vasectomy pain, genitofemoral neuralgia and other pain originating from the testicles, groin, or abdomen are common reasons for referral to a urological specialist. The incidence of patients with CTP, also referred to as orchialgia, orchidynia, or chronic scrotal pain, is large and may be caused by on-going inflammation of the testicle (orchitis) or epididymis (epdidymitis), trauma, tumors, hernia, torsion (twisting of the testicle), varicocele, hydrocele, spermatocele polyarteritis nodosa, and previous surgical interventions such as vasectomy and hernia surgery.

As an example, CTP or genitofemoral neuralgia may be attributed to nerve injury, such as stretching of a nerve, electrocoagulation, stricture caused by ligation, entrapment of the nerve in scar tissue, or irritation because of proximity to a zone of inflammation, during inguinal herniorrhaphy. The pain experienced by the patient may be unilateral or bilateral, constant or intermittent, spontaneous or exacerbated by physical activities and pressure, and may remain localized in the scrotum or radiate to the groin, perineum, back, or legs.

Typically, testicle removal and spermatic cord denervation procedures are used to treat CTP. In spermatic cord denervation procedures, nerves in or adjacent to the spermatic cord, i.e., the genitofemoral nerve or sympathetic nerves, are severed or permanently removed. Such procedures may result in permanent and substantial pain relief regardless of the origin of pain. However, severing or removing these nerves may result in loss of sensation in the testicle and/or scrotum, loss of the cremasteric reflex which may cause fertility issues, and even loss of blood flow causing the testicle to die. Therapeutic nerve blocks may also be used to treat CTP, but generally only relieve pain temporarily.

In addition, women may experience various types of sources of pelvic pain. Sources of pain may include injury to nerves resulting from surgical procedures, non-surgical conditions, vulvodynia which can be very debilitating but has no obvious source, and interstitial cystitis (painful bladder syndrome). Interstitial cystitis may be a source of pelvic pain in both women and men. Surgical procedures that may injure nerves in the pelvic region may include urological operations in the pelvic area, gynecological surgery, and hysterectomy. Non-surgical conditions which cause pain in women include adhesions, endometriosis, and pelvic congestion.

SUMMARY

In general, the invention is directed to techniques for applying electrical stimulation to a genitofemoral nerve or a genital nerve branch of the genitofemoral nerve of a patient via an implantable electrical stimulation device to alleviate symptoms of chronic pelvic pain in men or women. Pelvic pain may include urogenital pain or other forms of pelvic pain. The electrical stimulation may be applied to one or both genitofemoral nerves. In addition, the electrical stimulation may be applied directly to the genital branch of one or both genitofemoral nerves or, in the case of male patients, indirectly via the spermatic cord which contains a portion of the genital nerve branch.

A system according to the invention may include one or more electrical stimulators that apply electrical stimulation to the genitofemoral nerve or the genital branch of the genitofemoral nerve, e.g., via the spermatic cord in a male patient, to alleviate chronic testicular pain (CTP) or other afflictions associated with pelvic pain, including pain originating from the testicles, groin, or abdomen, such as post vasectomy pain and genitofemoral neuralgia. In female patients, an electrical stimulator delivers the stimulation to the genitofemoral nerve or genital nerve branch to alleviate other types of pelvic pain such as vulvodynia, interstitial cystitis, post-operative pain, adhesions, endometriosis or pelvic congestion.

The electrical stimulators may comprise various types of electrodes such as cuff electrodes, electrode leads, and/or microstimulators implanted at various locations proximate to one or both of the genitofemoral nerves of a patient or the genital branch of one or both genitofemoral nerves. The electrical stimulators may alternatively or additionally be implanted proximate to the genital branch of one or both genitofemoral nerves of a patient, e.g., directly or via the spermatic cord. In this manner, stimulation may be applied uni-laterally (to one cord or branch) or bi-laterally (to both cords or branches).

In some embodiments, electrical stimulation electrodes may be coupled to an implantable stimulation device implanted within a subcutaneous pocket in the abdomen or buttock of the patient or, alternatively, the scrotum of the patient. The electrical stimulation electrodes may be coupled to the implantable medical device via standard implantable electrode leads. Alternatively, leadless microstimulators may be positioned adjacent the target cords or nerves. In this case, the leadless microstimulators may be capable of wireless communication with other implantable medical devices, an external programmer, or both.

For male patients, stimulation electrodes or leadless microstimulators may be implanted using well known surgical procedures for exposing the spermatic cord, e.g., inguinal incision as used for spermatic cord denervation or hernia repair. Systems including such electrodes or microstimulators and employing the techniques described in this disclosure may substantially reduce or eliminate chronic pelvic pain, including urogenital pain such as CTP, without loss of sensation in the testicles and/or scrotum or loss of the cremasteric reflex as is common with testicle removal and spermatic cord denervation procedures.

Systems according to the invention may include an external programmer that programs the electrical stimulators to apply electrical stimulation to a genitofemoral nerve or genital nerve branch, e.g., directly or via a respective spermatic cord. During stimulation, a clinician or patient may operate the external programmer to adjust stimulation parameters, such as amplitude, pulse width, pulse rate, and electrode polarities. In some cases, a patient may use the programmer to deliver stimulation on demand, e.g., when the patient experiences discomfort. Additionally or alternatively, the implantable stimulation device may store stimulation programs and schedules. In this manner, the electrical stimulation can be delivered according to preprogrammed stimulation parameters and schedules, if desired.

In one embodiment, the invention provides a method comprising applying electrical stimulation to a genital nerve branch of a genitofemoral nerve of a patient via an implanted electrical stimulation device.

In another embodiment, the invention provides a system comprising an implantable electrical stimulation device that generates electrical stimulation selected to alleviate pelvic pain, and an electrode coupled to the electrical stimulation device at a position adjacent to a genital nerve branch of a genitofemoral nerve a patient.

In a further embodiment, the invention provides a method comprising applying electrical stimulation to at least a portion of a genitofemoral nerve of a patient via an implanted electrical stimulation device.

In another embodiment, the invention provides a system comprising an implantable electrical stimulation device that generates electrical stimulation selected to alleviate pelvic pain, and an electrode coupled to the electrical stimulation device at a position adjacent to a genitofemoral nerve of a patient.

In various embodiments, the invention may provide one or more advantages. For example, applying electrical stimulation to a genitofemoral nerve of a patient may substantially reduce or eliminate pelvic pain such as that caused by chronic testicular pain (CTP), post vasectomy pain, genitofemoral neuralgia, and other conditions that cause long term pain in the testicles, groin, or abdomen, as well as other forms of pelvic pain experienced by female patients.

Testicle removal and spermatic cord denervation procedures that sever nerves in or adjacent to the spermatic cord, i.e., a genital branch of the genitofemoral nerve, ilioinguinal nerve, or sympathetic nerves, often result in unwanted side effects including loss of sensation in the testicles and/or scrotum and loss of the cremasteric reflex which may cause fertility issues. Therapeutic nerve blocks typically only relieve pain temporarily. In contrast, delivery of electrical stimulation to one or both genital nerve branches, either directly or via the respective spermatic cords, may provide permanent or long-lived effective therapy for many patients with fewer or no unwanted side effects.

In addition, for male patients, electrical stimulators may be implanted proximate to the spermatic cord using well known surgical procedures for exposing the spermatic cord, e.g., inguinal incision as used for spermatic cord denervation or hernia repair, providing ease of deployment by experienced surgeons or other caregivers.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIGS. 11A-C are schematic diagrams illustrating an example leadless microstimulator suitable for use in the system of FIGS. 7 and 8.

DETAILED DESCRIPTION

Figure 1:
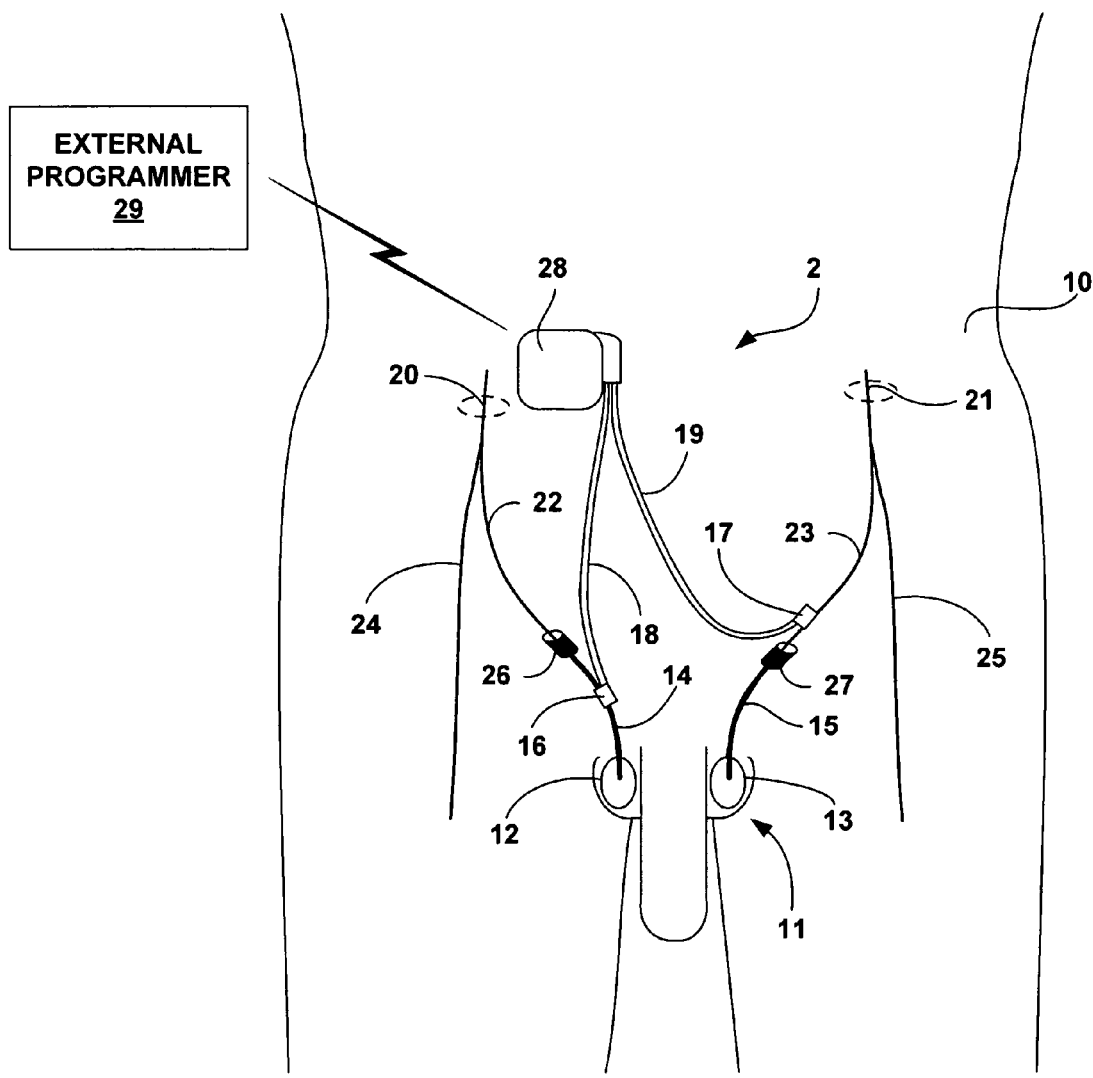
FIG. 1 is a schematic diagram illustrating an example system that includes an implantable stimulation device for applying electrical stimulation to a genital nerve branch of a patient for alleviation of pelvic pain from a front view of a male patient.

FIG. 1 is a schematic diagram illustrating an example system 2 that includes an implantable medical device (IMD) 28 in the form of an electrical stimulator that applies electrical stimulation to one or both genitofemoral nerves or the genital branch of one or both genitofemoral nerves, either directly or via spermatic cords 14 and 15 of a patient 10. In FIG. 1, system 2 is illustrated from a front view perspective of patient 10. Of course, application of stimulation to spermatic cords 14, 15 applies only in the case of male patients. Although the invention may be generally applicable to treat pelvic pain in both men and women, application of the invention to men will be described throughout this disclosure for purposes of illustration. Throughout the figures accompanying this disclosure, various anatomical features of patient 12 and structural features of system 2 are illustrated conceptually for ease of illustration. Accordingly, the figures may not necessarily present appropriate scales and proportions of such anatomical features. Rather, the drawings are indicated as a conceptual rendering of such features to aid in the understanding of pertinent embodiments of the invention.

In the example of FIG. 1, IMD 28 applies electrical stimulation to patient 10 for alleviation of chronic testicular pain (CTP), post vasectomy pain, genitofemoral neuralgia, and other conditions that cause long term (chronic) pain in the testicles (in a male patient), groin, or abdomen. CTP may be caused by on-going inflammation of the testicle (orchitis) or epididymis (epdidymitis), trauma, tumors, hernia, torsion (twisting of the testicle), varicocele, hydrocele, spermatocele polyarteritis nodosa, and previous surgical interventions such as vasectomy and hernia surgery. As an example, CTP or genitofemoral neuralgia may be attributed to nerve injury, such as stretching of a nerve, electrocoagulation, stricture caused by ligation, entrapment of the nerve in scar tissue, or irritation because of proximity to a zone of inflammation, during inguinal herniorrhaphy. In particular, damage to the genitofemoral nerve and, more particularly, the genital branch of the genitofemoral nerve may cause a patient to experience pain in the testicles or associated scrotal area. Stimulation parameters such as amplitude, pulse width and pulse rate may be selected as appropriate to alleviate pain for the particular patient 10.

In additional embodiments, IMD 28 applies electrical stimulation to a female patient (not shown) for alleviation of pelvic pain such as, urogenital pain. Examples of pain include pain resulting from surgical procedures, non-surgical procedures, vulvodynia, and interstitial cystitis (painful bladder syndrome). Nerve injury may be caused by various surgical procedures including urological operations in the pelvic area, gynecological surgery, and hysterectomy. Non-surgical condition which cause pain in women include adhesions, endometriosis, and pelvic congestion. For male or female patients, the pain may be idiopathic in origin. Applying electrical stimulation to the genitofemoral nerve or genital branch of the genitofemoral nerve in accordance with selected stimulation parameters may alleviate pain experienced by female patients.

FIG. 1 illustrates genital branches 22, 23 and femoral branches 24, 25 of genitofemoral nerves 20, 21, respectively. Generally, for a male patient, IMD 28 delivers electrical stimulation to spermatic cords 14 and 15 via electrodes which may be coupled to IMD 28 by one or more leads to block pain signals from testicles 12 and 13 and the associated scrotal area 11 from reaching the central nervous system (CNS). As shown in the illustrated example of FIG. 1, the electrodes may be configured to at least partially engage a portion of the genital nerve branch or spermatic cord. However, the invention is not so limited. Rather, the invention also includes embodiments in which electrodes may be implanted proximate to genitofemoral nerves 20, 21, i.e., above the branch point of genital nerve branches 22, 23, respectively. In the illustrated example of FIG. 1, a dotted circle indicates an example stimulation site along genitofemoral nerve 20, 21.

Further, the invention includes embodiments in which an electrode is implanted proximate to at least one of genitofemoral nerve 20, genitofemoral nerve 21, genital nerve branch 22, genital nerve branch 23, spermatic cord 14, and spermatic cord 15. For example, electrodes may be implanted proximate to genitofemoral nerve 20 and proximate to genital nerve branch 22. In another example, electrodes may be implanted proximate to genitofemoral nerve 20 and proximate to spermatic cord 14. In yet another example, electrodes may be implanted proximate to genital nerve branch 22 and proximate to spermatic cord 14. The invention further includes embodiments in which electrodes are implanted bi-laterally in any combination. Such embodiments are included without exhaustively listing all possible combinations. Accordingly, the positions of electrodes 16 and 17 in FIG. 1 is merely exemplary.

The pain experienced by the patient may be unilateral or bilateral, constant or intermittent, spontaneous or exacerbated by physical activities and pressure, and may remain localized or radiate outward. In a male patient, for example, testicular pain may remain localized in the scrotum or radiate to the groin, perineum, back, or legs. Delivering electrical stimulation causes parasthesia in testicles 12 and 13 and associated scrotal region 11 based on the position of the electrodes. The number and position of the leads is largely dependent on the pain perceived by the patient and the type of electrical stimulation delivered to treat the pain. Additionally, the leads coupled to IMD 28 may include various types of electrodes depending on the type of stimulation delivered and the location of the lead.

In the illustrated example, IMD 28 is coupled to leads 18 and 19. Leads 18, 19 may carry conventional ring electrodes, a paddle electrode array, or other types of electrodes. In the example of FIG. 1, leads 18 and 19 each include a cuff electrode, i.e., cuff electrodes 16 and 17, that delivers electrical stimulation therapy to spermatic cords 14 and 15, respectively. A cuff electrode includes a cuff-like fixation structure and one or more electrodes carried by the fixation structure. In the example of FIG. 1, leads 18 and 19 are implanted at different locations along spermatic cords 14 and 15, respectively. As a result, patient 10 may experience parasthesia in different areas on each side of his body in response to electrical stimulation delivered by electrodes 16 and 17.

Again, the invention is not limited to embodiments in which IMD 28 is coupled to cuff electrodes. Instead, IMD 28 may be coupled to any number and any type of electrodes, such as conventional ring electrode leads, paddle electrode leads, and other electrodes suitable for delivering electrical stimulation to the spermatic cord. In addition, in some cases, leadless stimulators may be used. Further, the invention is not limited to embodiments that deliver electrical stimulation to a specific area of the spermatic cord.

Figure 7:
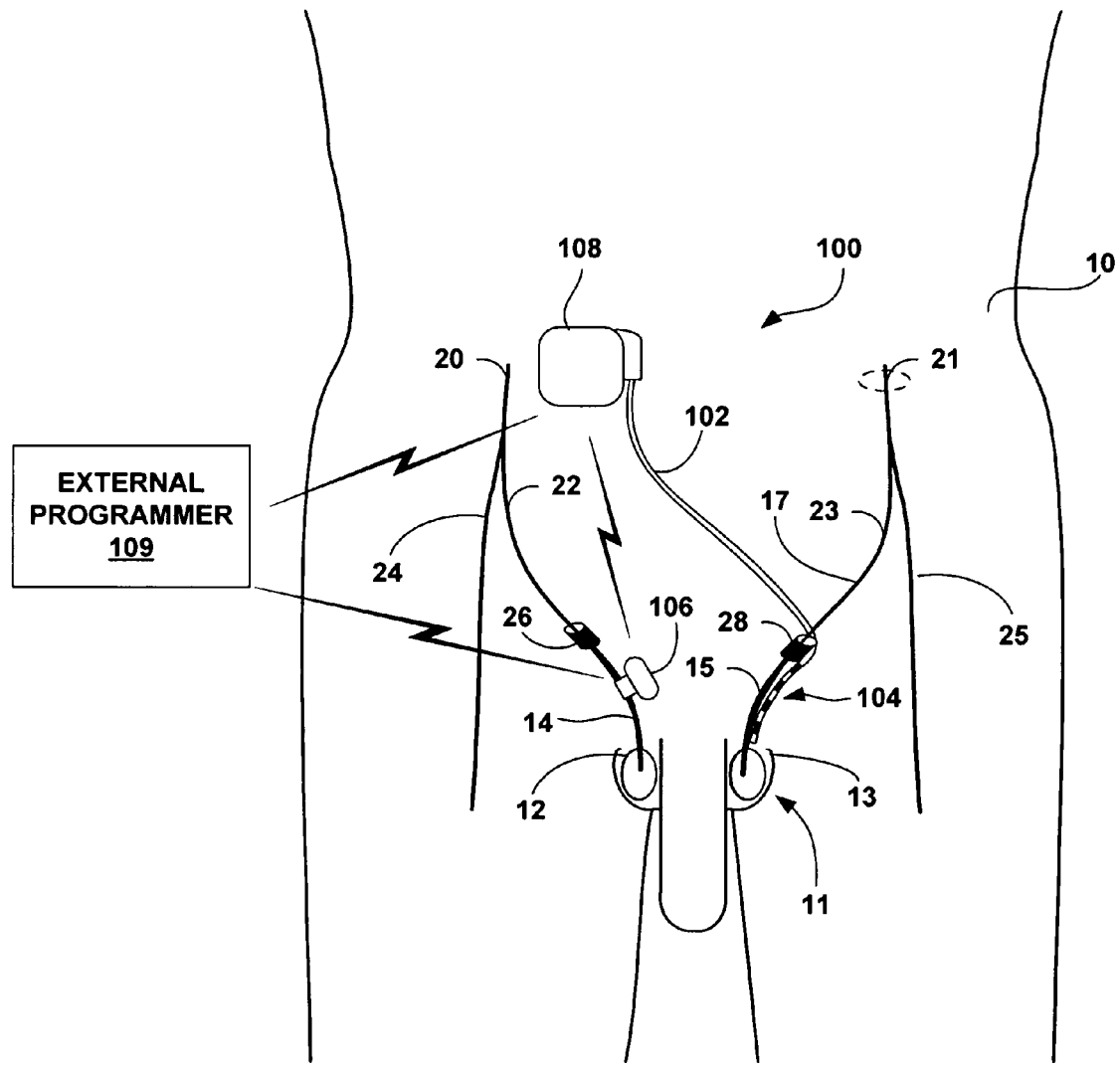
FIG. 7 is a schematic diagram illustrating another example system including two different types of electrical stimulators for applying electrical stimulation to a genital nerve branch of a patient from a front view of a male patient.

As an example, FIG. 7 illustrates another example system in which an IMD is coupled to an electrode lead having electrodes displaced on the distal end of the lead to stimulate a genital nerve branch of a patient, either directly or via a spermatic cord. FIG. 7 also illustrates a leadless microstimulator implanted within the fascia of a spermatic cord. In this case, an IMD or external programmer may wirelessly control the leadless microstimulator to deliver electrical stimulation to the fascia of the spermatic cord. In addition, although not illustrated, an IMD may also be coupled to an electrode suitable for applying electrical stimulation to the genitofemoral nerve.

With further reference to FIG. 1, IMD 28 may be coupled to deliver electrical stimulation energy to spermatic cords 14, 15 via cuff electrodes 16, 17, respectively. Cuff electrodes 16 and 17 each may comprise a rigid cuff electrode, a self-sizing spiral cuff electrode, a half cuff electrode, a helical electrode, a chambered electrode, or other types of cuff electrodes that are shaped, sized and otherwise configured to at least partially wrap around a spermatic cord. The cuff electrode may be sized and shaped to at least partially enclose the spermatic cord and promote electrical coupling pressure between the electrode and the fascia of the spermatic cord. The cuff electrodes 16, 17 may each include a single electrode or multiple electrodes. For example, a cuff electrode 16, 17 may include a bipolar or multipolar arrangement of electrodes or a unipolar electrode that is referenced to the electrical potential of an active can electrode carried by IMD 28.

IMD 28 includes electrical stimulation pulse generator circuitry and delivers electrical stimulation in the form of electrical pulses in accordance with stored stimulation parameters, e.g., electrode polarity, pulse amplitudes, pulse widths, and pulse rates. By way of example, the electrical stimulation may include stimulation pulses having pulse widths between approximately 10 and 5000 microseconds, more preferably between approximately 100 and 1000 microseconds and still more preferably between 180 and 450 microseconds. The stimulation pulses may define voltage amplitudes between approximately 0.1 and 50 volts, more preferably between approximately 0.5 and 20 volts and still more preferably between approximately 1 and 10 volts. The pulses may define frequencies between approximately 0.5 and 500 hertz, more preferably between approximately 10 and 250 hertz and still more preferably between approximately 50 and 150 hertz. The pulses may be alternating current (ac) pulses or direct current (dc) pulses, and may be mono-phasic, bi-phasic, or multi-phasic in various embodiments.

IMD 28 may drive electrodes 16 and 17 with the same or different stimulation pulses or waveforms. In some embodiments, IMD 28 may cause electrodes 16 and 17 to deliver electrical stimulation simultaneously, or in an interleaved or alternating fashion. For example, electrodes 16 and 17 may deliver electrical stimulation with different pulse rates, duty cycles or scheduled times for delivery, which may result in alternating delivery of stimulation. Interleaved or alternating delivery of stimulation may, for example, reduce the likelihood that neural accommodation or tolerance will impair the efficacy of the stimulation. Interleaved or alternating delivery of stimulation may also result in more complete pain relief than would be possible through delivery of stimulation via only one electrode or electrode array.

Leads 18 and 19 may be implanted proximate to spermatic cords 14 and 15, respectively. In the illustrated example, lead 18 is implanted proximate to spermatic cord 14 and lead 19 is implanted proximate to the genital branch 23 of genitofemoral nerve 21, but the invention is not limited as such. Rather, lead 18 may be implanted at various locations along spermatic cord 14, genital nerve branch 22, genitofemoral nerve 20, or sympathetic nerves (not shown). Spermatic cord 14 includes a lower portion of the genital nerve branch 22 of the genitofemoral nerve 20. Similarly, lead 19 may be implanted at various locations along spermatic cords 15, genital nerve branches 23, genitofemoral nerves 21, or sympathetic nerves (not shown). The positions of leads 18 and 19 in FIG. 1 are shown for purposes of illustration to show different possible implantation locations and associated target stimulation sites. Specifically, leads 18 and 19 illustrate two locations which may be particularly advantageous for applying electrical stimulation, which will be described in detail below. However, IMD 28 may be coupled to a single lead or a plurality of leads based on the perceived pain of the patient and his response to electrical stimulation therapy.

In FIG. 1, spermatic cords 14 and 15, genitofemoral nerves 20 and 21, and genital branches 22, 23 and femoral branches 24, 25 of genitofemoral nerves 20 and 21 are illustrated. FIG. 1 also illustrates inguinal canals 26 and 27. However, the genitofemoral nerve 20, 21 originates from the L1 and L2 nerves in the lumbar region (lower back) at L1/L2. As the genitofemoral nerve 20, 21 passes through the lumbar region, it crosses behind the ureter (not shown). Slightly posterior to and at a variable distance above the inguinal ligament (not shown), the genitofemoral nerve 20, 21 divides into the genital branches 22, 23 and femoral branches 24, 25. The genital branches 22, 23 cross the transverses abdominus (not shown) and internal oblique muscles (not shown) and enter the respective inguinal canal 26, 27 through the internal inguinal ring.

Within the inguinal canal 26, 27, the genital branch 22, 23 runs along the spermatic cord 14, 15, respectively. The spermatic cord includes various layers (not shown). These layers are the external spermatic fascia, cremasteric muscle and fascia, genitofemoral nerve, internal spermatic fascia, ductus deferens, lymph vessels, pampiniform plexus of veins which become the testicular vein, and testicular artery. More specifically, as the structures within the spermatic cord pass through the transversalis fascia (not shown), they join with one of the layers of the spermatic cord, the internal spermatic fascia.

As the spermatic cord 14, 15 continues through the inguinal canal, it joins with the cremasteric layer of muscle and fascia from the internal oblique muscle. These muscle fibers perform an important reflex, i.e., the cremasteric reflex. When the cremasteric muscle contracts, the testicle is pulled closer to the body. This reflex keeps the testicles at the correct temperature, for example, by relaxing when the testicles are too warm and contracting when the testicles are too cold. If the cremasteric reflex is absent or functions incorrectly, e.g., due to denervation or resection, the male may experience fertility related issues.

Finally, when the spermatic cord 14, 15 passes through the superficial ring, it joins an external spermatic fascia layer derived from the aponeurosis of the external oblique. After the spermatic cord 14, 15 traverses the inquinal canal 26, 27, it leads into the scrotum and to the testes 12, 13 where the genital branch 22, 23 of the genitofemoral nerve innervates the testes 12, 13. Electrical stimulation may be delivered via electrodes positioned proximate to the spermatic cord superior to a testicle and inferior to an inguinal canal of the patient, or positioned proximate to a genital branch of the genitofemoral nerve superior to an inguinal canal and inferior to the genitofemoral nerve of the patient.

In the illustrated example, cuff electrode 16 is wrapped around the external fascia of spermatic cord 14 and connected to IMD 28 via lead 18 and, optionally, a lead extension (not shown). The electrical stimulation applied by cuff electrode 16 stimulates the genital branch 22 of genitofemoral nerve 20 through the fascia. The fascia protects genital nerve branch 22 within spermatic cord 14 from being in direct contact with the cuff electrode, thus avoiding adhesion. Adhesion may be undesirable because the nerve may become damaged as the patient moves or if the electrode is removed. Thus, it may be desirable to deliver electrical stimulation to the spermatic cord by wrapping a cuff electrode around the spermatic cord below the inguinal canal and above the attached testicle, as shown in FIG. 1 with respect to electrode 16.

Electrode 17, in the illustrated example, also comprises a cuff electrode. More specifically, cuff electrode 17 is wrapped around genital nerve branch 23 above inguinal canal 27 and below genitofemoral nerve 21. Because cuff electrode 17 is located higher (upstream in the central nervous system) from cuff electrode 16, patient 10 may experience parasthesia over a larger area, which may be advantageous in some instances. However, genital nerve branch 23 does not include an external fascia to serve as a protective layer in this region. Consequently, wrapping cuff electrode 17 around genital nerve branch 23 may inherently have a greater risk of pinching or otherwise damaging the nerve, possibly reducing the long-term efficacy of the electrical stimulation. As a result, additional care may be necessary when wrapping a cuff electrode around the genital nerve branch above the inguinal canal and below the genitofemoral nerve, as shown with respect to electrode 17.

The positions of electrodes 16, 17 in FIG. 1 are for purposes of illustration of different possible positions. In practice, one or both electrodes 16, 17 may be positioned above inguinal canal 27 and below genitofemoral nerve 21 to directly stimulate genital nerve branch 23. Alternatively, one or both electrodes 16, 17 may be positioned below inguinal canal 27 and above testes 12, 13 to indirectly stimulate genital nerve branch 23 indirectly via spermatic cord 15. As discussed previously, electrodes may be positioned based on the pain perceived by the patient and the type of electrical stimulation delivered to treat the pain. In general, to treat pelvic pain such as CTP, electrodes may be implanted proximate to the spermatic cord above or below the inguinal canal to apply electrical stimulation to the genital branch of the genitofemoral nerve or proximate to the genitofemoral nerve to apply electrical stimulation to the genitofemoral nerve.

In general, it may be difficult to wrap a cuff electrode around the spermatic cord within the inguinal canal. Furthermore, it may not be desirable to apply electrical stimulation to the spermatic cord within the inguinal canal because the spermatic cord joins the cremasteric muscle as it passes through the inguinal canal. Consequently, stimulating the spermatic cord within the inguinal canal may result in unwanted triggering of the cremasteric reflex.

Leads 18 and 19 are typically either surgically implanted or inserted percutaneously. Leads 18 and 19 may be surgically implanted using well known surgical techniques. For example, the surgical procedure for exposing the spermatic cord is well defined, i.e., inguinal incision as used for spermatic cord denervation or hernia repair. A surgical procedure for genitofemoral neurectomy is described in detail in Judith A. Murovic et. al, "Surgical Management of 10 Genitofemoral Neuralgias at the Louisiana State University Health Sciences Center," Neurosurgery, Volume 56, Number 2, pages 298-303, February 2005. A procedure for spermatic cord denervation is described in detail in Laurence A. Levine et al., Microsurgical Denervation of the Spermatic Cord as Primary Surgical Treatment of Chronic Orchialgia, The Journal of Urology, Vol. 165, pages 1927-1929, June 2001. Prior to surgically implanting electrodes, local nerve blocks may be performed using a nerve blocking agent to determine the precise nerve involved in the pain experienced by the patient. If a spermatic nerve block ameliorates the patient's pain, a surgeon may conclude that electrical nerve stimulation is likely to be efficacious, and may proceed to surgically implant electrodes in accordance with the invention. Alternatively, a clinician may stimulate the patient using an insulated needle to determine the nerve involved and the placement of an electrode. The diagnosis may also be made using the results of the patient history, physical examination, and preoperative electromyography.

IMD 28 may be implanted at a site in patient 10 near spermatic cords 14 and 15. The implantation site may be a subcutaneous location in the side of the lower abdomen or the buttock. Alternatively, IMD 28 may be implanted within the scrotum of the patient. In this case, IMD 28 may be miniaturized to allow IMD 28 to be implanted within the scrotum. In any case, the surgeon may then tunnel a lead through tissue and subsequently connect the lead to IMD 28, with or without a lead extension. IMD 28 may be constructed with a biocompatible housing, such as titanium or stainless steel, much like a conventional neurostimulator such as those used for spinal cord stimulation or pelvic stimulation, e.g., for relief of chronic pain, sexual dysfunction, or urinary or fecal incontinence.

External programmer 29 may control delivery of electrical stimulation by IMD 28. For example, in some embodiments, external programmer 28 may comprise a clinician programmer or a patient programmer. A clinician programmer may be a handheld computing device including a display, such as an LCD or LED display, to display electrical stimulation parameters. A clinician programmer may also include a keypad, which may be used by a user to interact with the clinician programmer. In some embodiments, the display may be a touch screen display, and a user may interact with the clinician programmer via the display. A user may also interact with the clinician programmer using peripheral pointing devices, such as a stylus or mouse. The keypad may take the form of an alphanumeric keypad or a reduced set of keys associated with particular functions.

A clinician (not shown) may use the clinician programmer to program electrical stimulation to be delivered to patient 10. In particular, the clinician may use the clinician programmer to select values for therapy parameters, such as pulse amplitude, pulse width, pulse rate, electrode polarity and duty cycle, for one of or both electrodes 16 and 17. IMD 28 may deliver the electrical stimulation according to programs, each program including values for a plurality of such therapy parameters. In this manner, IMD 28 controls delivery of electrical stimulation according to preprogrammed stimulation programs and schedules.

When implemented as a patient programmer, external programmer 29 may be a handheld computing device. The patient programmer 26 may also include a display and a keypad to allow patient 10 to interact with the patient programmer. In some embodiments, the display may be a touch screen display, and patient 10 may interact with the patient programmer via the display. Patient 10 may also interact with the patient programmer using peripheral pointing devices, such as a stylus or mouse.

Patient 10 may use the patient programmer to control the delivery of electrical stimulation. In particular, in response to a command from patient 10, external programmer 29 may activate IMD 28 to deliver electrical stimulation or, alternatively, deactivate IMD 28 when no electrical stimulation is desired. Patient 10 may also use the patient programmer to select the programs that will be used by IMD 28 to deliver electrical stimulation. Further, patient 10 may use the patient programmer to make adjustments to programs, such as adjustments to amplitude, pulse width and/or pulse rate. Additionally, the clinician or patient 10 may use a clinician or patient programmer to create or adjust schedules for delivery of electrical stimulation.

IMD 28 and external programmer 29, implemented as a clinician programmer or a patient programmer, communicate via wireless communication. In some embodiments, external programmer 29 communicates via wireless communication with IMD 28 using radio frequency (RF) telemetry techniques known in the art. The clinician programmer and patient programmer may communicate with one another by wireless communication, e.g., to change or update programs. Alternatively, the programmers may communicate via a wired connection, such as via a serial communication cable, or via exchange of removable media, such as magnetic or optical disks, or memory cards.

As previously described, leads 18 and 19 may be implanted surgically or percutaneously. When inserted percutaneously, leads 18 and 19 may be used in conjunction with an external trial stimulator (not shown) in order to determine if permanent implantation of the electrodes and leads is an effective treatment for the patient's pain. For example, prior to implantation of IMD 28, patient 10 may engage in a trial period, in which patient 10 receives an external trial stimulator on a temporary basis. The external trial stimulator is coupled to implanted leads via a percutaneous lead extension. As an alternative, one or more temporary leads may be used for trial stimulation, instead of chronic leads, which are implanted if trial stimulation is effective.

The trial neurostimulation permits a clinician to observe neurostimulation efficacy and determine whether implantation of a chronic neurostimulation device is advisable. Specifically, the trial neurostimulation period may assist the clinician in selecting values for a number of programmable parameters in order to define the neurostimulation therapy delivered to patient 10. For example, the clinician may select an amplitude, which may be current- or voltage-controlled, and pulse width for a stimulation waveform to be delivered to patient 10, as well as a rate, i.e., frequency) delivered to the patient. In addition, the clinician also selects particular electrodes on a lead to be used to deliver the pulses, and the polarities of the selected electrodes.

By stimulating nerves associated with the spermatic cord, a system in accordance with an embodiment of the invention may substantially reduce or eliminate pelvic pain such as CTP, post vasectomy pain, genitofemoral neuralgia, and other conditions that cause long term pain in the testicles, groin, or abdomen. Testicle removal and spermatic cord denervation procedures may result in permanent and substantial pain relief but may also cause unwanted side effects, such as loss of sensation in the testicle and/or scrotum, loss of the cremasteric reflex which may cause fertility issues, and even loss of blood flow causing the testicle to die. Therapeutic nerve blocks may also be used to treat CTP, but generally only relieve pain temporarily. Because electrical stimulation does not require severing any nerves associated with the spermatic cord and, more particularly, aims to avoid damaging nerves, the invention may provide similar or improved pain relief without the unwanted side effects.

Figure 2:
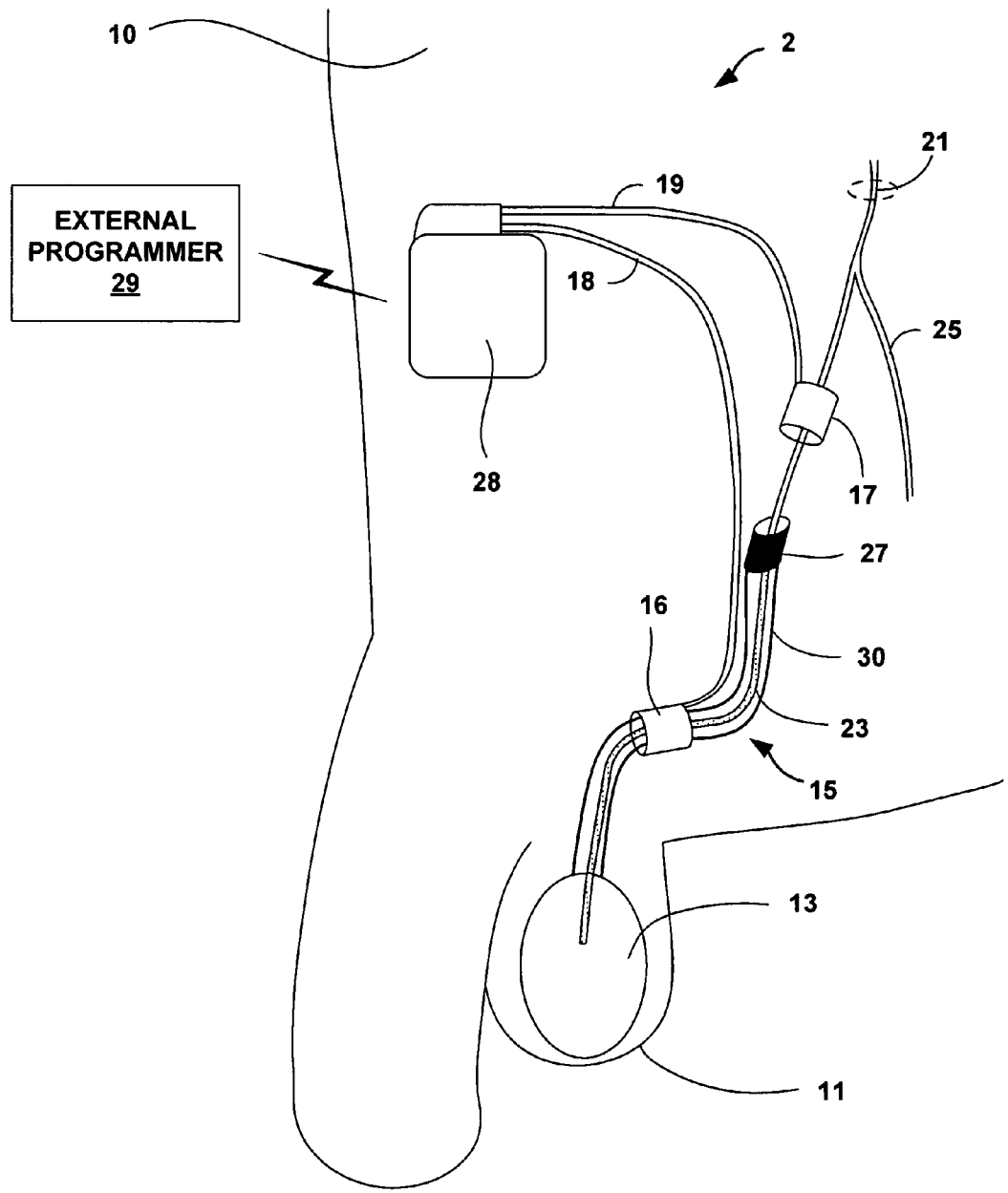
FIG. 2 is a schematic diagram further illustrating the example system of FIG. 1 from a side view of a male patient.

FIG. 2 is a schematic diagram further illustrating system 2. In particular, system 2 is illustrated from the left side of patient 10. For purposes of illustration, only spermatic cord 15, genital nerve branch 23, femoral nerve branch 25, genitofemoral nerve 21, and testicle 13 are shown. Furthermore, cuff electrode 16 is illustrated as being wrapped around spermatic cord 15 to illustrate the different locations at which electrodes may be implanted and to illustrate an embodiment in which multiple electrodes are implanted along a single spermatic cord 15. Accordingly, cuff electrode 17 is shown as being wrapped around genital nerve branch 23, while cuff electrode 16 is shown as being wrapped around spermatic cord 15. Following the convention illustrated in FIG. 1, a dotted circle illustrates an example stimulation site at which an electrode may be implanted proximate to genitofemoral nerve 21 in combination with one or more of electrodes 16 and 17. In an embodiment in which two or more electrodes are implanted along the same spermatic cord, the electrodes may form a bipolar pair that is referenced between the two electrodes, or be individually referenced to an electrical potential associated with IMD 28. Also, in some embodiments, multiple cuffs or leads may be implanted along a single spermatic cord 15, and each may carry multiple electrodes, e.g., in an axial or planar array, providing still more possible electrode combinations for selection by a physician.

FIG. 2 illustrates genital nerve branch 23 originating from genitofemoral nerve 21 and passing through inguinal canal 27 to innervate testicle 13. As previously described, spermatic cord 15 joins an external fascia layer 30 as it passes through the superficial ring of the inguinal canal. Genital nerve branch 23 is shown within the external fascia 30 of spermatic cord 15. Cuff electrode 16 is wrapped around external fascia 30 of spermatic cord 15. External fascia 30 may serve to protect genital nerve branch from being damaged when cuff electrode 16 is implanted. In particular, external fascia 30 prevents cuff electrode 16 from being in direct contact with genital nerve branch 23 which may result in a more pleasant paresthesia because electrical stimulation is delivered to genital nerve branch 23 indirectly. Additionally, as mentioned previously, external fascia 30 may provide a buffer that reduces the damage to genital nerve branch 23 when patient 10 moves. For example, external fascia 30 may act as a cushion that prevents cuff electrode 16 from pinching, stretching, or otherwise damaging genital nerve branch 23 as patient 10 moves.

In general, cuff electrodes 16 and 17 may be particularly advantageous because cuff electrodes 16 and 17 may remain in place as patient 10 moves without requiring any external fixation means such as sutures or anchoring mechanisms. External fixation means may damage tissue or the nerve itself, possibly causing additional pain which may reduce the efficacy of the electrical stimulation therapy. Cuff electrodes 16 and 17 include a fixation structure that at least partially wraps around spermatic cord 15 and genital nerve branch 23, respectively. The fixation structure may be fabricated from a flexible biocompatible material that provides a flexible interface between the electrode and the tissue, i.e., spermatic cord 15 or genital nerve branch 23. In some embodiments, the fixation structure may be fabricated from a rigid biocompatible material. In such cases, the fixation structure may form a split cylinder or a "U" shape sized to fit around the spermatic cord or genital nerve branch. Cuff electrodes 16 and 17 may generally comprise a rigid cuff electrode, a self-sizing spiral cuff electrode, a half cuff electrode, a helical electrode, a chambered electrode, and other types of cuff electrodes that at least partially wrap around a spermatic cord. Upon enclosure of at least a portion of the spermatic cord, a cuff may be held in a closed position by shape memory properties, sutures, interlocking tabs, surgical adhesive, crimping, or other fixation techniques or structures.

Figure 3A:
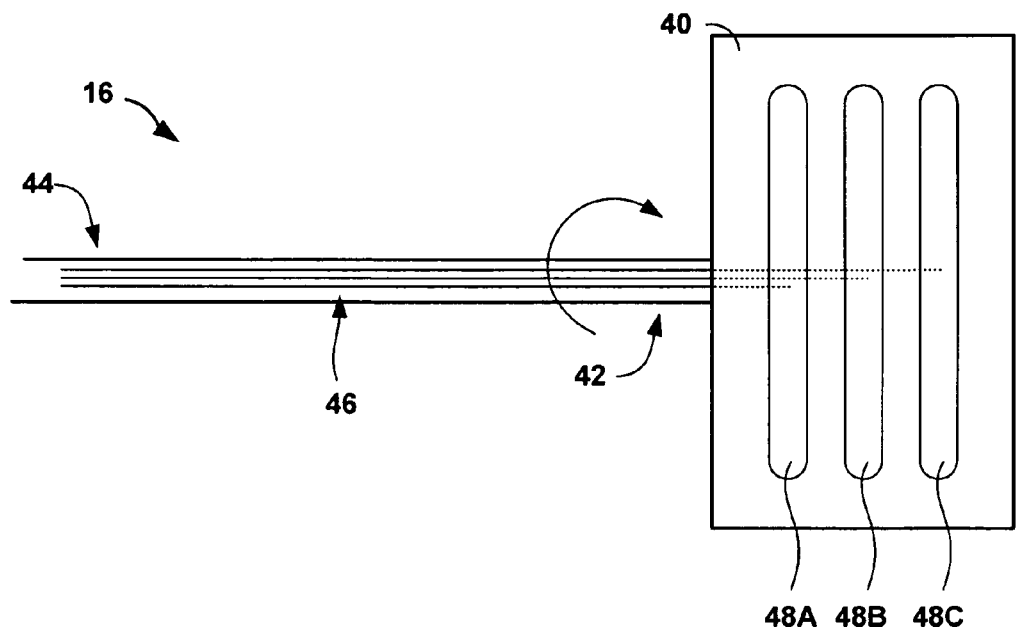
FIGS. 3A-C are schematic diagrams illustrating an example cuff electrode useful in the system of FIGS. 1 and 2.
Figure 3B:
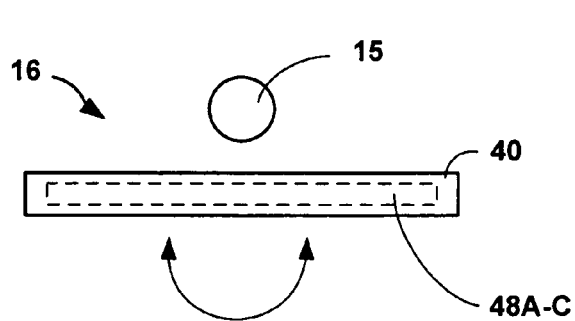
Figure 3C:
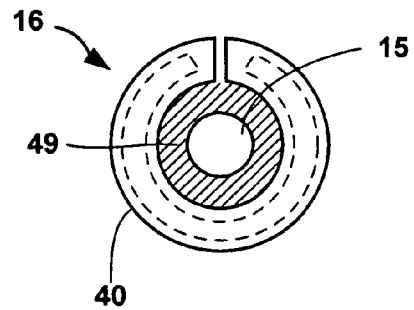

FIGS. 3A-C are schematic diagrams illustrating an exemplary embodiment of a cuff electrode 16. Cuff electrode 17 may be similarly constructed. Cuff electrodes 16 and 17 may be any type of cuff electrode used to deliver electrical stimulation. In some embodiments, cuff electrodes 16 and 17 may both comprise the same type of cuff electrode or may comprise different types of cuff electrodes. In any case, cuff electrode 16 is merely exemplary and should not be considered limiting of the invention as broadly embodied and described in this disclosure. The purpose of FIGS. 3A-C is to illustrate the implantation of cuff electrodes to deliver electrical stimulation to the spermatic cord and genital branch of the genitofemoral nerve.

FIG. 3A is a top view of cuff electrode 16. Cuff electrode 16 includes lead 18, fixation structure 40, a plurality of stimulation electrodes 48A-C, and a plurality of electrical conductors 46 and 47 within lead 18. Conductor 46 may comprise one or more supply wires 46 that deliver electrical stimulation therapy to one or more electrodes. In the example of FIG. 3A, cuff electrode 16 includes three electrodes 48A, 48B, 48C. In the illustrated example, electrodes 48A-C are arranged such that a major axis of each electrode extends laterally to the spermatic cord. In this manner, the length of each electrode may be wrapped about all or a portion of the circumference of the spermatic cord. The proximal end 44 of lead 18 is connected to IMD 28 and fixation structure 40 is attached to the distal end 42 of lead 18.

Cuff electrode 16 may generally include one electrode or a plurality of electrodes. Each of electrodes 48A-C is coupled to one of supply conductors 46. Electrodes 118A-C may be driven together with a common conductor or independently via separate conductors 46. When electrodes 48A-C are driven by a common conductor, they may be referenced to one or more electrodes carried by another lead or one or more electrodes carried by the IMD housing. When electrodes 48A-C are driven by separate conductors, bipolar or multipolar electrode combinations may be formed on a single lead or among two or more leads, as well as between one or more leads and the IMD housing.

For a given bipolar pair of electrodes on a lead, one supply conductor sources stimulation energy to a first electrode and a second supply conductor sinks stimulation energy from a second electrode, with the stimulation energy propagating across nerve tissue between the first and second electrodes. Hence, one electrode may form a cathode while the other forms an anode. Also, in some embodiments, multiple anodes and cathodes may be used in an electrode combination. A switch device in the IMD determines which electrodes will function as cathodes and which electrodes will function as anodes.

As previously described, fixation structure 40 may be fabricated from a flexible biocompatible material that provides a flexible interface between the electrode and the spermatic cord genital nerve branch. In some embodiments, fixation structure 40 may be fabricated from a rigid biocompatible material. The rigid fixation structure may form a split cylinder or a "U" shape sized to fit around the spermatic cord or genital nerve branch. In any case, when implanting electrode 16, the surgeon may elevate the spermatic cord and wrap fixation structure 40 around the spermatic cord or genital nerve branch. The manner in which the surgeon installs the cuff electrode around the spermatic cord or genital nerve branch depends on the type of cuff electrode. For example, if fixation structure 40 is fabricated from a shape memory alloy, fixation structure 40 may recover its shape at a fixed temperature, e.g., slightly under room temperature. By sufficiently cooling fixation structure 40, the surgeon can easily open the cuff and position fixation structure 40 under the spermatic cord. Because the nominal body temperature of the patient is above room temperature, fixation structure 40 warms up and recovers its initial shape thereby closing or wrapping fixation structure 40 around the spermatic cord.

A cuff electrode may provide more direct electrical contact with a nerve than a standard ring or paddle electrode lead. However, in some cases, applying electrical stimulation directly to a nerve may result in the patient experiencing an unpleasant sensation, such as a burning sensation. Consequently, a standard electrode implanted proximate to the target nerve may be advantageous because the patient may experience a more pleasant paresthesia as a result of stimulation. In addition, a standard electrode lead may also be advantageous in terms of surgical ease of implantation.

FIG. 3B is a cross sectional view of cuff electrode 16 implanted underneath spermatic cord 15. In the illustrated example, fixation structure 40 is flat thereby allowing the surgeon to easily position electrode 16 under spermatic cord 15. When fixation structure 40 is fabricated from a shape memory alloy material, such as Nitinol, the surgeon may cool fixation structure 40 prior to positioning fixation structure 40 to easily manipulate fixation structure 40 into the open configuration shown in FIG. 3B. The surgeon may then position fixation structure under spermatic cord 15. Fixation structure 40 will recover its initial shape, i.e., a substantially closed ring sized to fit around spermatic cord 15, as fixation structure warms up to its activation temperature.

FIG. 3C is a cross sectional via of cuff electrode 16 implanted and wrapped around spermatic cord 15. More specifically, FIG. 3C illustrates the shape of fixation structure 40 when it has returned to its initial shape in response to warming from the patient's body heat. In the illustrated example, a gap 49 exists between spermatic cord 15 and fixation structure 40. The gap may be filled with tissue or fluids and may provide a buffer that prevents cuff electrode 16 from damaging spermatic cord 15. Alternatively, fixation structure 40 may be sized to wrap around spermatic cord 15 such that there is no gap between fixation structure 40 and spermatic cord 15. In some embodiments, fixation structure may be deployed used superelastic properties of a shape memory allow such as Nitinol. For example, the fixation structure may be constrained in a flat shape either manually or with a surgical took, and then released so that it wraps around the nerve.

Figure 4:
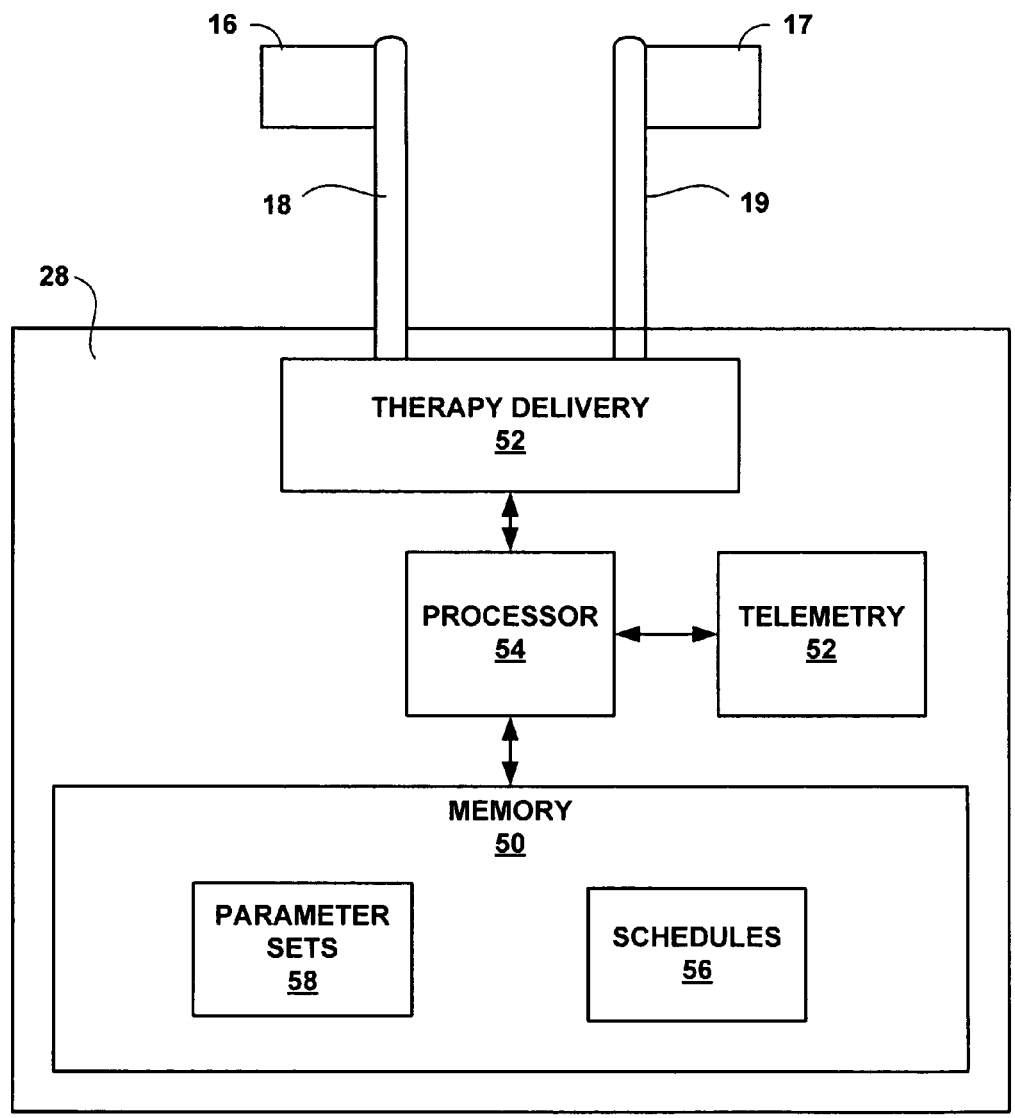
FIG. 4 is a block diagram illustrating an example implantable stimulation device for applying electrical stimulation to the genital nerve branch of a patient.

FIG. 4 is a block diagram illustrating an example configuration of IMD 28. IMD 28 may apply electrical stimulation to spermatic cord 14 and genital branch 23 of the genitofemoral nerve 21 of patient 10 via cuff electrodes 16 and 17 coupled to IMD 28 via leads 18 and 19, respectively. The configuration, type, and number of electrodes illustrated in FIG. 4 are merely exemplary. Leadless stimulators alternatively may be used instead of or in addition to leads 18, 19 and cuff electrodes 16, 17. A leadless stimulator does not generally include any elongated leads, and instead carries electrodes on a housing of the stimulator or on a structure such as a fixation device extending from the housing.

In the example of FIG. 4, cuff electrodes 16 and 17 are electrically coupled to a therapy delivery module 52 via leads 18 and 19, respectively. Therapy delivery module 52 may, for example, include an output pulse generator coupled to a power source such as a battery and charge storage capacitor. Therapy delivery module 52 may deliver electrical stimulation pulses to patient 10 via one or both of electrodes 16 and 17 under the control of a processor 54.

Processor 54 controls therapy delivery module 52 to deliver electrical stimulation according to a selected parameter set stored in memory 56. Specifically, processor 54 may control circuit 52 to deliver electrical stimulation pulses with the amplitudes and widths, and at the rates specified by the programs of the selected parameter set. Processor 54 may also control circuit 52 to deliver each pulse according to a different program of the parameter set. Processor 54 may include a microprocessor, a controller, a digital signal processor (DSP), an application specific integrated circuit (ASIC), a field programmable gate array (FPGA), or any other equivalent integrated or discrete logic circuitry, or the like.

In some embodiments, memory 50 may store parameter sets 58 that are available to be selected by patient 10 for delivery of electrical stimulation. Memory 50 may also store schedules 56. Memory 50 may include any combination of volatile, non-volatile, fixed, removable, magnetic, optical, or solid state media, such as a random access memory (RAM), random access memory (ROM), CD-ROM, hard disk, removable magnetic disk, memory cards, non-volatile RAM (NVRAM), electrically programmable ROM (EEPROM), flash memory, and the like.

IMD 28 delivers stimulation according to preprogrammed stimulation parameters and, optionally, schedules stored in memory 50. Schedules 56 may define times for processor 54 to select particular parameter sets 58 and control therapy delivery module to delivery therapy according to that parameter set. A schedule 56 may cause electrical stimulation to be delivered via electrodes 16 and 17 at respective times, which may include simultaneous and/or alternate delivery. For example, stimulation may be activated, deactivated or altered for different times of the day, such as times during which the patient is awake or sleeping, or working or at rest. A clinician or patient may create, modify, and select schedules 56 using external programmer 29.

IMD 28 also includes a telemetry circuit 53 that allows processor 54 to communicate with external programmer 29, i.e., a clinician programmer or patient programmer. Processor 54 may receive programs to test on patient 10 from external programmer 29 via telemetry circuit 52 during programming by a clinician. Where IMD 28 stores parameter sets 58 in memory 50, processor 54 may receive parameter sets 58 from external programmer 29 via telemetry circuit 52 during programming by a clinician, and later receive parameter set selections made by patient 10 from external programmer 29 via telemetry circuit 52. Where external programmer 29 stores the parameter sets, processor 54 may receive parameter sets selected by patient 10 from external programmer 29 via telemetry circuit 52.

Figure 5:
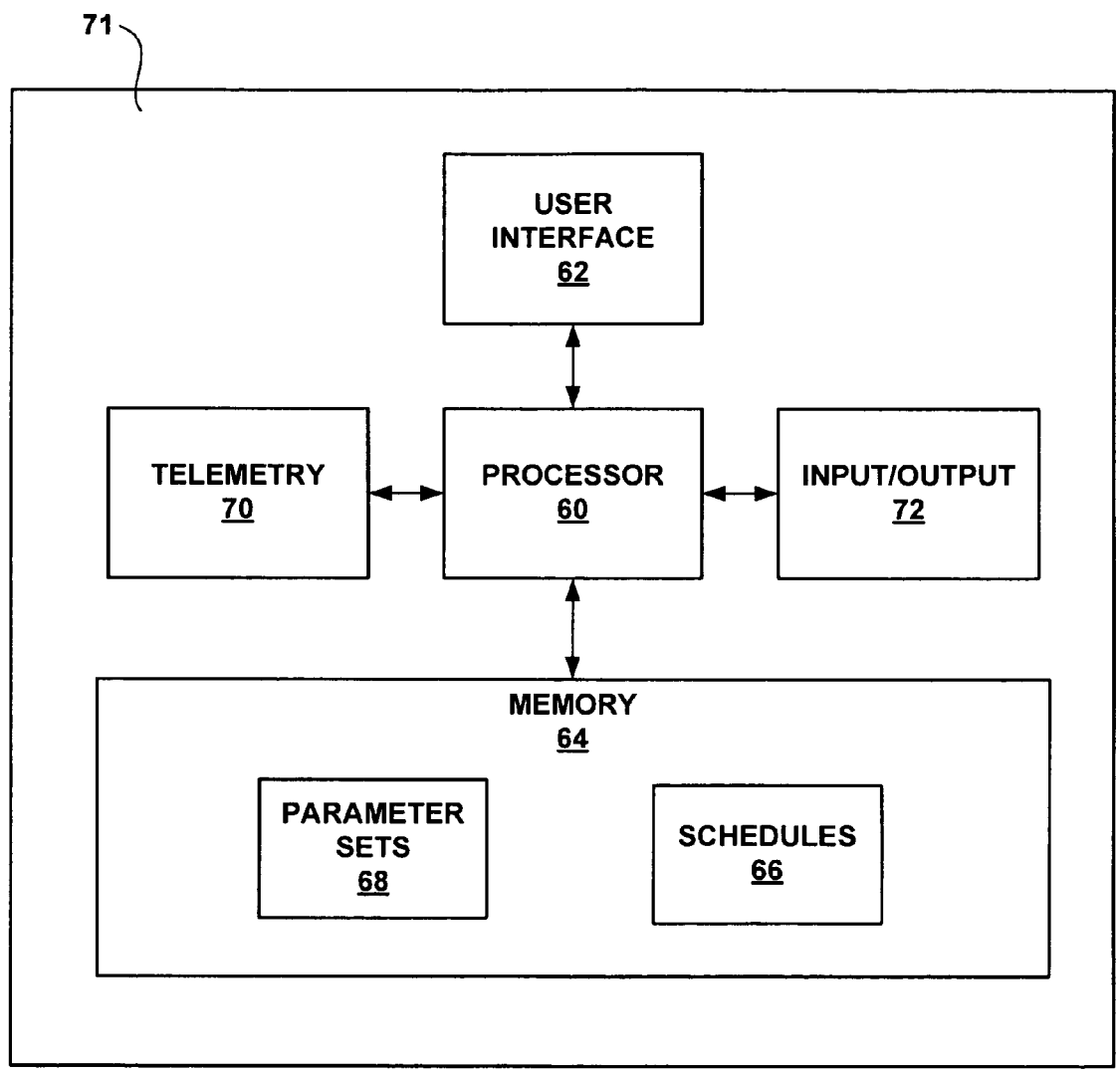
FIG. 5 is a block diagram illustrating an example clinician programmer that allows a clinician to program electrical stimulation therapy for a patient.

FIG. 5 is a block diagram illustrating an example patient programmer 71 that allows a clinician to program electrical stimulation therapy for a patient. Patient 10 may interact with a processor 60 via a user interface 62 in order to control delivery of electrical therapy as described herein. User interface 62 may include a display and a keypad, and may also include a touch screen or peripheral pointing devices as described above. Processor 60 may also provide a graphical user interface (GUI) to facilitate interaction with patient 10, as will be described in greater detail below. Processor 60 may include a microprocessor, a controller, a DSP, an ASIC, an FPGA, discrete logic circuitry, or the like.

Patient programmer 71 also includes a memory 64. In some embodiments, memory 64 may store parameter sets 68 that are available to be selected by patient 10 for delivery of electrical stimulation. Memory 64 may also store schedules 66. Hence, parameter sets and schedules may be stored in IMD 28, patient programmer 71, or both. Patient programmer 71 also includes a telemetry circuit 70 that allows processor 60 to communicate with IMD 28, and, optionally, input/output circuitry 72 that to allow processor 60 to communicate with a clinician programmer.

Processor 60 may receive parameter set selections made by patient 10 via user interface 62, and may either transmit the selection or the selected parameter set to IMD 28 via telemetry circuitry 70 for delivery of electrical stimulation according to the selected parameter set. Where patient programmer 71 stores parameter sets 66 in memory 64, processor 60 may receive parameter sets 66 from a clinician programmer via input/output circuitry 72 during programming by a clinician. Circuitry 72 may include transceivers for wireless communication, appropriate ports for wired communication or communication via removable electrical media, or appropriate drives for communication via removable magnetic or optical media.

Figure 6:
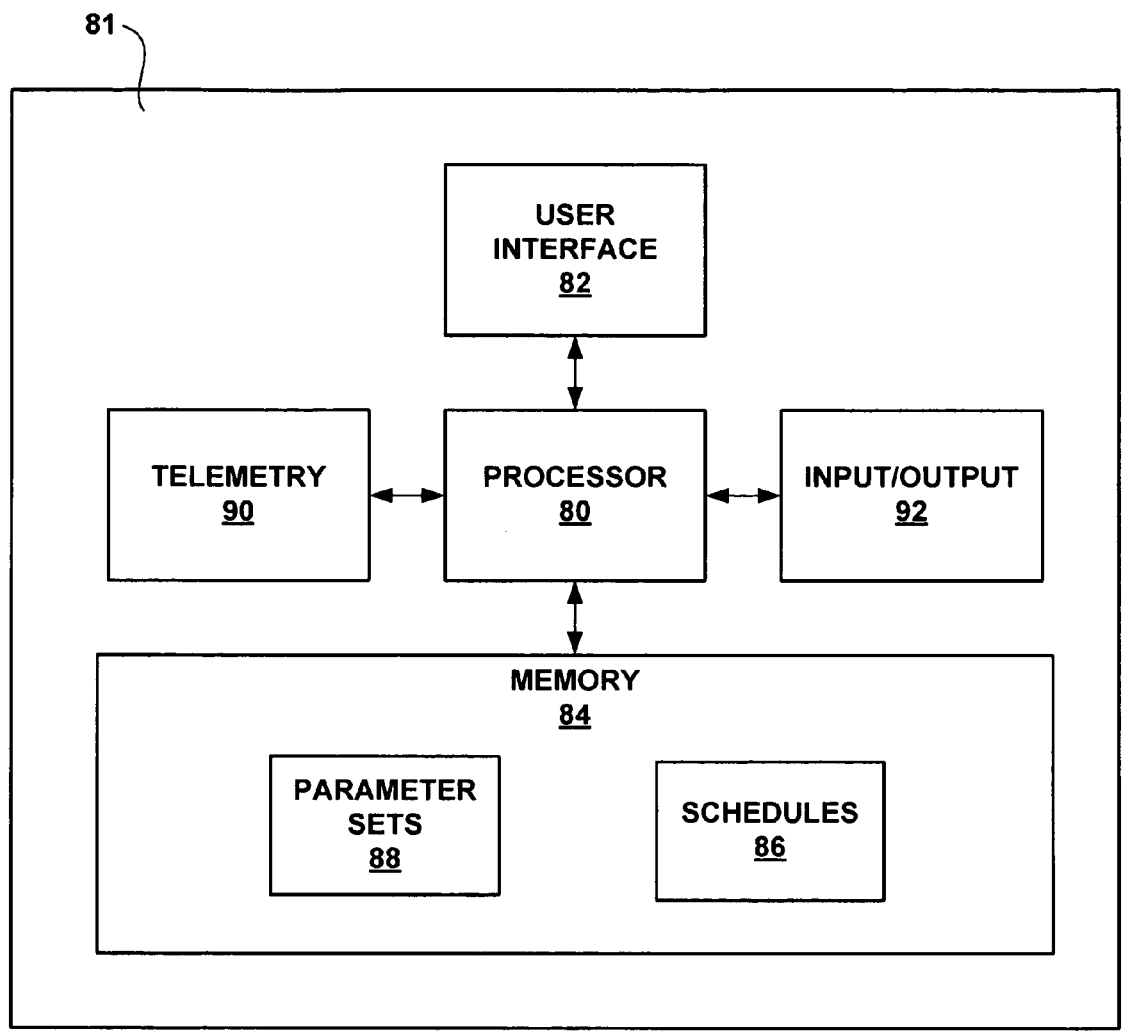
FIG. 6 is a block diagram illustrating an example patient programmer that allows a patient to control delivery of electrical stimulation.

FIG. 6 is a block diagram illustrating an example clinician programmer 81 that allows a clinician to control delivery of electrical stimulation. A clinician may interact with a processor 80 via a user interface 82 in order to program delivery of electrical stimulation as described herein. User interface 82 may include a display and a keypad, and may also include a touch screen or peripheral pointing devices as described above. Processor 80 may also provide a graphical user interface (GUI) to facilitate interaction with a clinician, as will be described in greater detail below. Processor 80 may include a microprocessor, a controller, a DSP, an ASIC, an FPGA, discrete logic circuitry, or the like.

Clinician programmer 81 also includes a memory 84 that stores parameter sets 88 and schedules 86. Parameter sets 88 may be made available to be selected by a clinician for delivery of electrical stimulation. Memory 84 may also store schedules 86 which cause electrical stimulation to be delivered via electrodes 16 and 17 at respective times. A clinician may program delivery of electrical stimulation by specifying parameter sets 86. The clinician may interact with the GUI and user interface 82 in order to specify parameter sets.

Processor 80 transmits the selected or specified parameter sets to IMD 28 for delivery to patient 10 via a telemetry circuit 88. Processor 80 may transmit parameter sets 86 and schedules 88 created by the clinician to IMD 28 via telemetry circuitry 88, or to patient programmer 71 via input/output circuitry 92. I/O circuitry 92 may include transceivers for wireless communication, appropriate ports for wired communication or communication via removable electrical media, or appropriate drives for communication via removable magnetic or optical media.

FIG. 7 is a schematic diagram illustrating an example system 100 for applying electrical stimulation to a male patient 10 for pelvic pain such as CTP, post vasectomy pain, genitofemoral neuralgia, and other conditions that cause long term (chronic) pain in the testicles, groin, or abdomen. System 100 also may be useful for alleviation of pelvic for female patients. In the illustrated example, system 100 includes electrodes 104 deployed on a lead extending from an IMD 108, and a leadless microstimulator 106. Electrodes 104 and leadless microstimulator 106 deliver electrical stimulation to spermatic cord 15 and 14, respectively, and illustrate alternative arrangements stimulation. Hence, stimulation energy may be delivered to spermatic cords 14, 15 via any combination of cuff electrodes, axial electrode arrays, planar electrode array (e.g., on paddle lead), leadless microstimulators, or other types of electrodes. As previously described, electrodes 104 and leadless microstimulator may, in some embodiments, be implanted proximate to genitofemoral nerve 21. Following the convention illustrated in FIGS. 1 and 2, a dotted circle illustrates an example stimulation site at which an electrodes 104 and microstimulator 106 may be implanted proximate to genitofemoral nerve 21.

IMD 108 controls the delivery of electrical stimulation according to preprogrammed stimulation programs, parameter sets and/or schedules. In particular, IMD 108 or external programmer 109 may wirelessly control microstimulator 106 to deliver electrical stimulation to spermatic cord 14. Alternatively, microstimulator 106 may operate autonomously or in a coordinated manner in conjunction with other microstimulators or IMD 108. In the example of FIG. 7, IMD 108 is also coupled to electrodes 104 via lead 102. Again, the invention is not limited to the illustrated configuration. In general, IMD 108 may be coupled to any number and type of electrodes or electrical stimulators. The electrodes may also be positioned adjacent to one or both spermatic cords 14, 15 based on the perceived pain of patient 10. However, FIG. 7 merely illustrates example system 100 in which microstimulator 106 and electrodes 104 deliver bi-lateral electrical stimulation to spermatic cords 14 and 15.

In the illustrated example, microstimulator 106 is implanted adjacent to spermatic cord 14 and includes a housing and a fixation structure attached to the housing. The housing may be formed into a capsule-like shape and may be constructed from any of a variety of biocompatible materials, such as titanium or stainless steel. As will be described, the housing may carry an implantable pulse generator (IPG) and, optionally, a telemetry interface to exchange (send, receive or both) control signals with other devices such as IMD 108 or external programmer 109. The fixation structure on microstimulator 106 may be constructed similar to the fixation structure of previously described cuff electrodes 16 and 17. For example, the fixation structure on microstimulator 106 may be constructed of a flexible or a rigid biocompatible material that at least partially wraps around spermatic cord 14. The fixation structure may carry one or more electrodes, i.e., the electrodes may be integrated with the fixation structure, and the housing may include short leads that extend from the housing to couple the electrodes to the housing.

Alternatively, leadless microstimulator 106 may be implanted within the external fascia of spermatic cord 14 using a needle (not shown). In particular, microstimulator 106 may be implanted with a minimally invasive, percutaneous procedure. As an example, the needle may include a hollow cylinder and a pointed distal end for puncturing skin of patient 10. The needle may include the microstimulator and a fluid, e.g., saline solution, or push rod to force the microstimulator out of the needle. In this case, microstimulator 106 may be miniaturized in order to be implanted using the needle. In some embodiments, a plurality of microstimulators may be implanted within the external fascia of the spermatic cord or in tissue proximate to the genital branch of the genitofemoral nerve. The plurality of implanted microstimulators may apply electrical stimulation independently or on a coordinated basis.

When implanted within the external fascia of the spermatic cord, microstimulator 106 may comprise a self-contained module. The module comprises a housing that may carry one or more electrodes and an IPG within the housing. The IPG may comprise a circuit board and a power source, such as a battery, to provide power to the circuit board and electrodes. The circuit board may include the telemetry interface and other processing electronics. The electrodes may be pads mounted on a surface of the housing or ring electrodes that extend about the entire periphery of the housing. In some cases, the housing itself may form an active "can" electrode in addition to the electrodes mounted on the housing.

Microstimulator 106 may be implanted with less invasive procedures than other electrodes that are coupled to an IMD via a lead. For example, because microstimulator 106 wirelessly communicates with IMD 108, a surgeon does not have to tunnel a lead to IMD 108. In some embodiments, microstimulator 106 may wirelessly communicate with external programmer 109. In this case, external programmer 109 may be a small, battery-powered, portable device that may accompany patient 10 through the day. External programmer 109 may have a simple user interface, such as a button or keypad, and a display or lights. Patient 10 may only be able to activate and deactivate IMD 108. However, in other embodiments, external programmer 109 may include additional functionality to operate in a manner similar to a patient programmer.

In the illustrated example, ring electrodes 104 mounted on lead 102 also may be used to deliver electrical stimulation to spermatic cord 15. Lead 102 is coupled to IMD 108 and caries electrical conductors to transmit stimulation energy from the IMD to the electrodes 104. Lead 102 may be implanted adjacent to spermatic cord 15 as shown. However, lead 102 may also be implanted adjacent to genital nerve branch 23 instead of, or in addition to, the illustrated location. Lead 102 is shown in FIG. 7 carrying four electrodes, e.g., ring electrodes, although any number of electrodes could be used. Also, as mentioned previously, electrodes 104 may be arranged in an axial array, e.g., as ring electrodes, or in a two-dimensional planar array, e.g., in a paddle lead. Also, other types of leads providing curved or rounded electrode arrays may be used. At least one conductor is included in lead 102 that electrically connects the proximal end of lead 102 to electrodes 104 in its distal end. IMD 108 may control electrical stimulation applied by each of electrodes 104 separately or control electrical stimulation applied by a group of electrodes 104.

In some embodiments, lead 102 may be formed to include fixation elements, such as hooks, barbs, helical structures, tissue ingrowth mechanisms, or other anchoring mechanisms, e.g., at a distal end of lead 102. Fixation elements may serve to fix electrodes 104, relative to spermatic cord 15 so that electrodes 104 can provide consistent electrical simulation. Without anchoring electrodes 104 to spermatic cord 15 or tissue proximate to spermatic cord 15, the distance between electrodes 104 and spermatic cord may vary as patient 10 moves throughout the day, reducing the efficacy of the applied electrical stimulation. However, is possible that anchoring mechanisms may damage the spermatic cord or surrounding tissue during implantation or as patient 10 moves.

System 100 generally operates in a similar manner to system 2 in FIG. 1 to apply electrical stimulation for CTP or other pelvic pain disorders. Accordingly, external programmer 109 may comprise a clinician programmer or a patient programmer. As shown, external programmer 109 may communicate via wireless communication with IMD 108 In particular, external programmer 109 may control delivery of electrical stimulation by IMD 108 using telemetry techniques known in the art. When microstimulator 106 comprises a self-contained module, external programmer 109 may directly communicate with microstimulator 106 via wireless communication to control delivery of electrical stimulation.

Rather than being implanted along a side of spermatic cord 15, in a direction substantially parallel to the path of the spermatic cord, electrodes 104 of lead 102 may be implanted substantially perpendicular to the spermatic cord. Implanting electrodes 104 perpendicular to spermatic cord 15 may provide certain advantages. For example, when implanted perpendicular, electrodes 104 may more effectively apply electrical stimulation to a point along spermatic cord 15 instead of applying electrical stimulation along a length or portion of the spermatic cord. Patient 10 may experience a more complete relief of pain or fewer unwanted side effects as a result of applying electrical stimulation in this manner. The invention is not limited to the illustrated embodiments. Instead, electrodes 104 may be implanted at any orientation with respect to spermatic cord 15.

Figure 8:
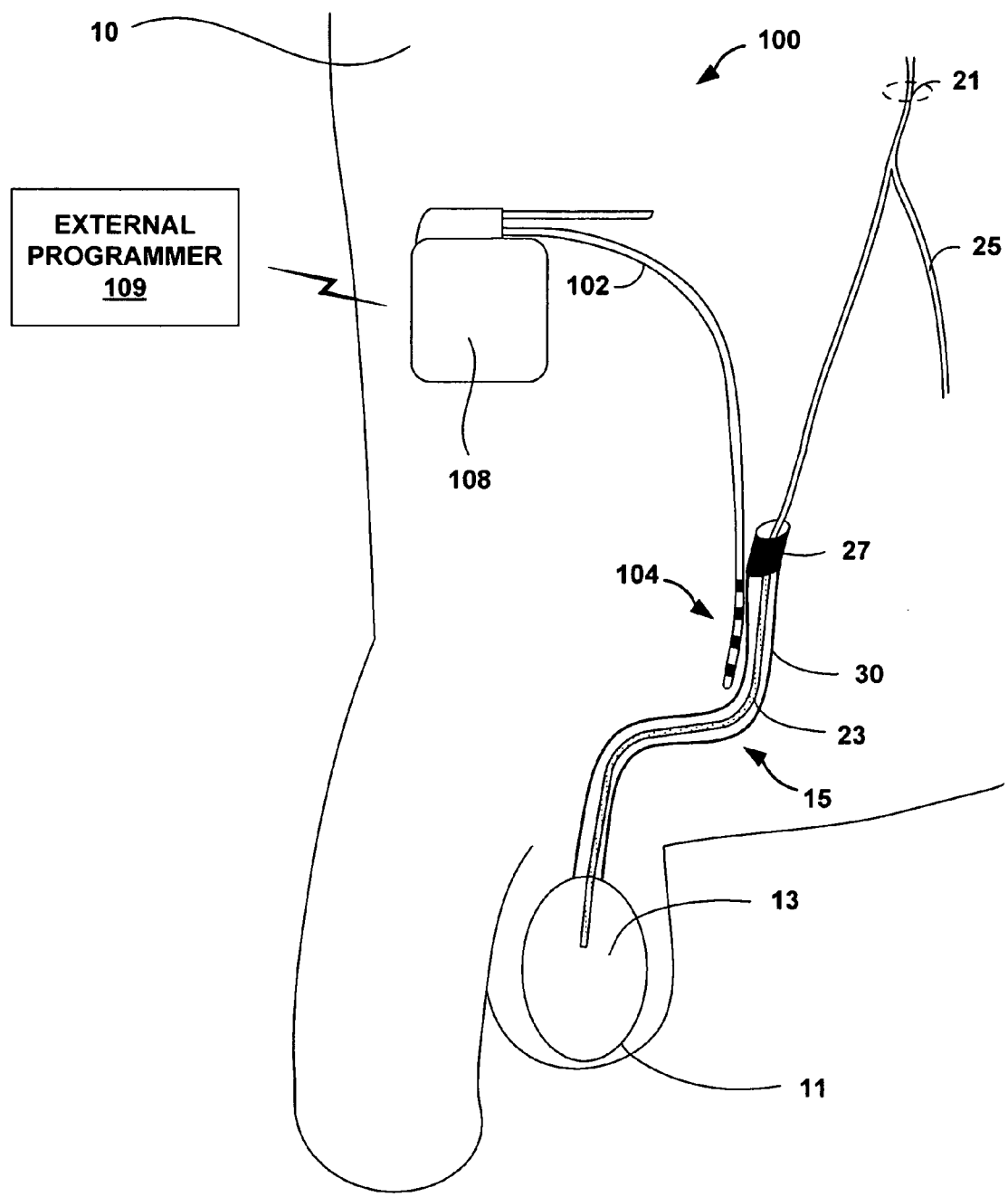
FIG. 8 is a schematic diagram further illustrating the example system of FIG. 7 from a side view of a male patient.

FIG. 8 is a schematic diagram further illustrating example system 100. In particular, system 100 is illustrated from the left side of a male patient 10 in FIG. 8. For purposes of illustration, only spermatic cord 15, genital nerve branch 23, femoral nerve branch 25, genitofemoral nerve 21, inguinal canal 27, and testicle 13 are shown. Again, genitofemoral nerve 21 originates from the L1 and L2 nerves in the lumbar region and divides into femoral branch 25 and genital branch 23. The dotted circle indicates an example stimulation site at which an electrode may be implanted to apply electrical stimulation to genitofemoral nerve 21. Femoral branch 25 supplies the skin over the femoral triangle (not shown) and communicates with the intermediate cutaneous nerve (not shown) of the thigh.

In general, electrical stimulation is applied to spermatic cord 15 through electrodes 104 of lead 102 implanted adjacent to spermatic cord 15. Electrodes 104 apply electrical stimulation to spermatic cord 15 under control of IMD 108. Lead 102 carries electrodes 104 and couples electrodes 104 to IMD 108. In particular, at least one electrical conductor is included in lead 102 that electrically connects electrodes 104 to IMD 108. Electrodes 104 may comprise four electrodes, e.g., ring electrodes, although the invention is not so limited. Electrodes 104 may comprise any number and type of electrodes. In some embodiments, as mentioned above, lead 102 may include fixation elements, such as hooks, barbs, helical structures, tissue ingrowth mechanisms, or other anchoring mechanisms that aid in securing lead 102 to spermatic cord 15 or tissue proximate to spermatic cord 15. Securing lead 102 to spermatic cord 15 or to tissue proximate to spermatic cord 15 may prevent lead 102 from moving relative to spermatic cord 15.

IMD 108 is programmed to deliver electrical stimulation appropriate for CTP, post vasectomy pain, genitofemoral neuralgia, and other conditions that cause long term (chronic) pain in the testicles, groin, or abdomen. IMD 108 may control electrical stimulation applied by each of electrodes 104 independently. Alternatively, IMD 108 may control electrical stimulation applied by a group of electrodes 104, and may select different combinations of electrodes 104 in bipolar or multi-polar arrangements to identify a particular combination that is most effective in producing desired parasthesia. Again, IMD 108 may control delivery of electrical stimulation according to parameter sets and/or schedules programmed in internal memory.

Although FIG. 8 illustrates lead 102 implanted adjacent to spermatic cord 15 below inguinal canal 27, lead 102 may be implanted adjacent to genital nerve branch 23 above inguinal canal 27. In this case, electrodes 104 may apply electrical stimulation to genital nerve branch 23 more directly. In addition, applying electrical stimulation to genital nerve branch 23 at a location further upstream may cause patient 10 to experience a larger area of paresthesia in response to electrical stimulation. In both male and female patients, stimulation may be applied close or below the inguinal canal 27.

Figure 9A:
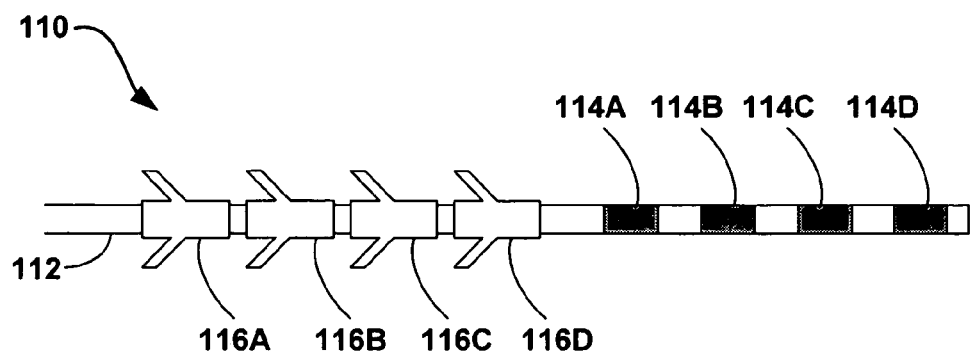
FIGS. 9A and 9B are schematic diagrams illustrating an example electrode lead of FIGS. 7 and 8.
Figure 9B:
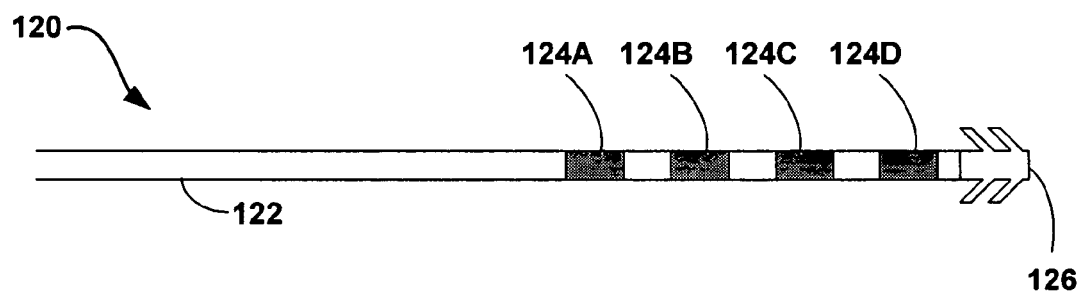

FIGS. 9A-C show exemplary electrical leads with fixation elements to secure the lead within a patient. As shown in FIG. 9A, lead 110 includes lead body 112, tines 116A-D (collectively tines 116) and electrodes 114A-D (collectively electrodes 114). Lead 110 may be a standard lead that includes all four tines 116 close to electrodes 114. Lead 110 may be implemented with any number of electrodes or tines. When implanting lead 110, having tines 116 close to electrodes 114 may be beneficial by allowing less movement of electrodes 114 with respect to the spermatic cord.

Electrodes 114 are more effective in delivering electrical stimulation when the electrodes are located close to the genital nerve branch spermatic cord. If electrodes 114 migrated away from the spermatic cord, due to movement of the patient throughout the day, for example, the efficacy of the stimulation may decrease. Therefore, tines 116 located close to electrodes 114 may be beneficial to therapy efficacy.

FIG. 9B illustrates a lead 120 which includes lead body 122, tines 126, and electrodes 124A-D (collectively electrodes 124). Lead 120 may be a standard lead that includes tines 126 located at the distal end of lead body 122. Lead 120 may be implemented with any number of electrodes or tines. Electrodes 124 may be located close to or a distance away from tines 126. When electrodes 124 are close to tines 126, implanting lead 120 may allow less movement of electrodes 124 with respect to the spermatic cord. Consequently, the intensity of electrical stimulation delivered to the spermatic cord may not vary and cause the patient to experience different levels of paresthesia.

When electrodes 124 are located a distance away from tines 126, implanting lead 102 may allow electrodes 124 to reach further away from the anchoring site. For example, when lead 102 delivers electrical stimulation to a genital branch of the genitofemoral nerve above the inguinal canal, i.e., before the genital nerve branch joins the spermatic cord, tines may be anchored to tissue a distance away from the genital nerve branch while leads may be located proximate to the genital nerve branch. Securing tines 126 to genital nerve branch is undesirable because the nerve may be damaged in the process. Thus, lead 120 may be beneficial by preventing unwanted nerve damage during the implantation process.

Figure 10:
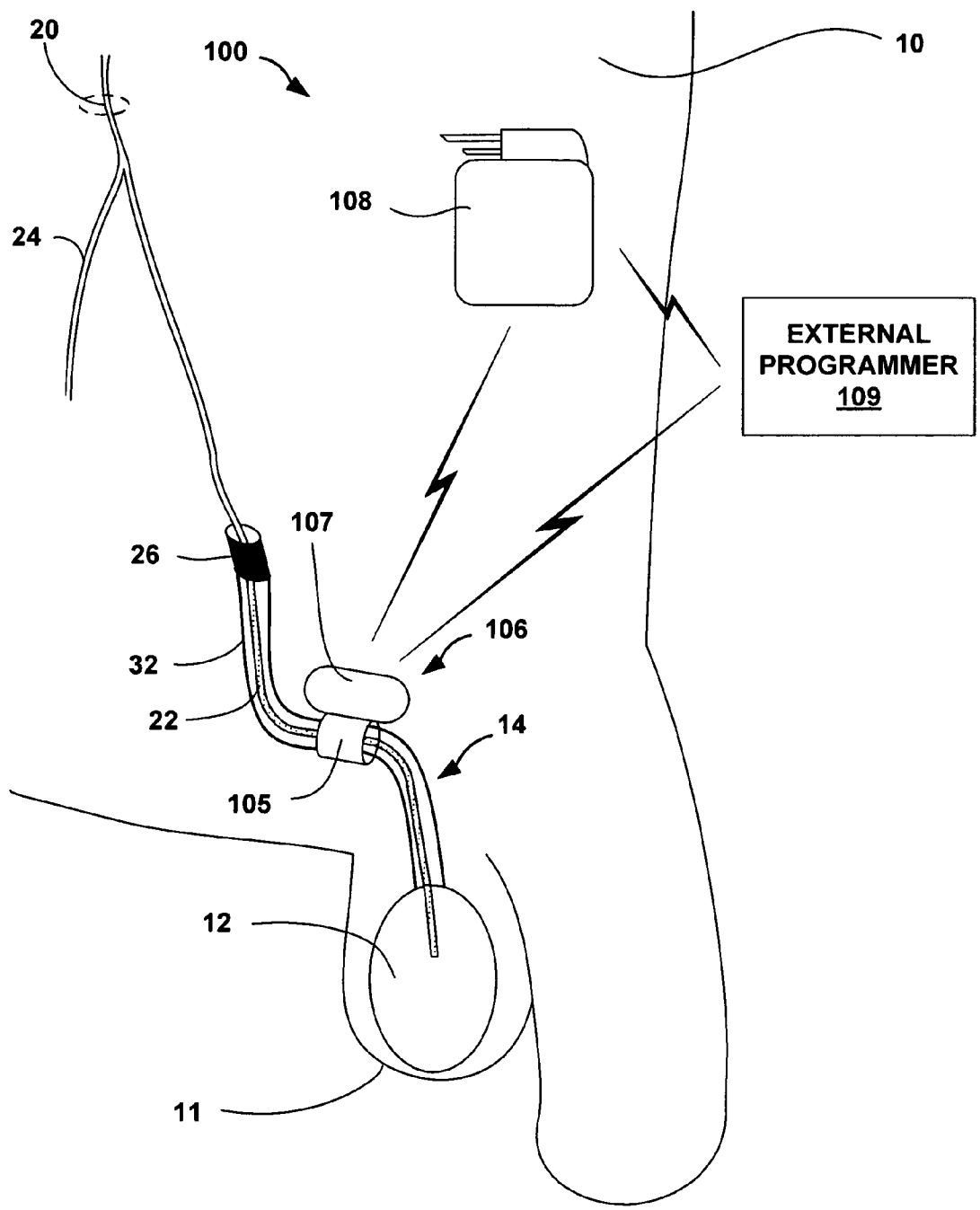
FIG. 10 is a schematic diagram further illustrating the example system of FIG. 7.

FIG. 10 is a schematic diagram further illustrating example system 100. In particular, system 100 is illustrated from the right side of a male patient 10. For purposes of illustration, only spermatic cord 14, genital nerve branch 22, femoral nerve branch 24, genitofemoral nerve 20, inguinal canal 26, and testicle 12 are shown. As previously described, spermatic cord 14 includes various layers and structures. For example, as spermatic cord 14 passes through inguinal canal 26, it joins the cremasteric layer of muscle and fascia responsible for the cremasteric reflex. Additionally, spermatic cord 14 picks up an external fascia layer 32 as it exits inguinal canal 26 through the superficial ring. Accordingly, genital branch 22 is shown within the external fascia 32 of spermatic cord 14.

Microstimulator 106 applies electrical stimulation to spermatic cord 14 under control of IMD 108 or external programmer 109. As shown, IMD 108 or external programmer 109 may wirelessly control microstimulator 106 to delivery electrical stimulation. Microelectrode 106 includes a housing 107 and a fixation structure 105, such as a cuff, attached to housing 107. Housing 107 may be formed into a capsule-like shape and may be constructed from any of a variety of biocompatible materials, such as titanium. Housing 107 may carry an IPG and a telemetry interface to receive control signals from IMD 108. Fixation structure 105 wraps at least partially around spermatic cord 14 to secure microstimulator 106 in place. Accordingly, fixation structure may operate and be constructed similar to the fixation structure of previously described cuff electrodes 16 and 17. Fixation structure 105 may carry one or more electrodes coupled to housing 107 via short leads (not shown). In some embodiments, housing 107 may form an active "can" electrode.

The invention is not limited to the illustrated configuration. For example, microstimulator 106 may also be implanted to deliver electrical stimulation to genital nerve branch 22 above inguinal canal 26. In this case, fixation structure 105 wraps at least partially around genital nerve branch 22. When applying electrical stimulation to genital nerve branch 22 before it joins spermatic cord 14, microstimulator 106 may be beneficial because it does not require fixation elements to secure it in place. In addition, in some embodiments, a microstimulator may implanted to deliver electrical stimulation at both locations in a coordinated manner or independently of each other. In further embodiments, a microstimulator 106 may also be implanted in proximate to genitofemoral nerve 20. Microstimulator 106 may be implanted proximate to genitofemoral nerve 20 using techniques similar to implanting microstimulator proximate to genital nerve branch 22. The dotted circle around genitofemoral nerve 20 indicates an example site at which microstimulator may be implanted.

FIGS. 11A-C are enlarged schematic diagrams showing microstimulator 106. In particular, FIG. 11A is an enlarged top view of microstimulator 106 including housing 107, circuit board 130, power supply 132, fixation structure 105, and electrodes 108A-C (collectively electrodes 108). Housing 107 may have a rounded, capsule-like shape, and a smooth, atraumatic surface formed of one or more biocompatible materials, such as titanium, stainless steel, epoxy, or polyvinylchloride. However, the invention is not so limited. Instead, housing 107 may have a shape that is compatible with the anatomy at the implant site, i.e., the spermatic cord or the genital nerve branch before it joins the spermatic cord. In some embodiments, the leadless microstimulator may have a capsule shape with a diameter of approximately less than or equal to 2 cm and a length of less than or equal to approximately 5 cm.

Fixation structure 105 may be constructed of a flexible or rigid biocompatible material that at least partially wraps around the spermatic cord or genital nerve branch, e.g., like a cuff. For example, fixation structure 105 may be fabricated from a shape memory alloy that has the capacity to recover a memorized shape when deformed at a certain temperature and then heated at a higher temperature or vice versa. In this case, the memorized shape may be a split cylinder or a substantially closed cylinder with a diameter sized to wrap around the spermatic nerve or genital nerve branch.

FIG. 11A illustrates fixation structure 105 in a deformed, generally open state that enables a surgeon to easily position slip microstimulator 106 underneath the spermatic cord. However, after positioning microstimulator 106 beneath the spermatic cord, the body temperature of the patient causes fixation structure 105 to recover its memorized shape, i.e., a split cylinder. Therefore, fixation structure 105 may be beneficial by reducing trauma during surgical implantation procedures.

Fixation structure 105 also carries one or more electrodes 108. Electrodes 108 may be driven together or independently. Electrodes 108 may be integrated with fixation structure 105 or, alternatively housing 107 may include short leads (not shown) that extend from housing 107 to couple electrodes 108 to housing 107.

Circuit board 130 may include a processor, memory, pulse generator circuitry to generate electrical pulses delivered by 108, and telemetry circuitry for wireless telemetry with IMD 108, external programmer 109, or both. As an example, the memory may store stimulation parameters, e.g., electrode polarity, pulse width, pulse rate, and amplitude. Memory may also may store schedules which define times for the processor to select particular parameters. A schedule may cause electrical stimulation to be delivered at respective times. In this manner, the processor may control the pulse generator circuitry generate electrical stimulation pulses in accordance with the selected parameters and schedule.

Microstimulator 106 may also operate under control from an external programmer, so that a physician or patient may activate, deactivate and/or modify stimulation delivered to the patient on a selective basis. Power source 132 supplies operating power to circuit board 130 and may take the form of a small rechargeable or non-rechargeable battery. Different types of batteries or different battery sizes may be used. To promote longevity, power source 132 may be rechargeable via induction or other means.

FIG. 11B illustrates a cross sectional view of microstimulator 106 implanted underneath spermatic cord 14. In the illustrated example, fixation structure 105 is flat, thereby allowing the surgeon to easily position microelectrode 106 underneath spermatic cord 14. When fabricated from an shape memory alloy, the body temperature of patient 10 may heat fixation structure 105 above the recovery shape temperature.

FIG. 11C is a cross sectional view of microelectrode 106 with fixations structure 105 wrapped substantially around spermatic cord 14. For example, as fixation structure 105 is warmed above its recovery shape temperature, fixation structure 105 recovers its initial shape, i.e., a substantially closed cylinder or ring. As shown in FIG. 11C, in some embodiments, fixation structure 105 may not close completely. However, fixation structure 105 may at least wrap partially around spermatic cord 14, or the genitofemoral nerve or genital nerve branch in order to secure microstimulator 106 to the nerve site. Removing microelectrode 106 may be easier when fixation structure 105 does not completely wrap around spermatic cord 14 because the gap between the ends of fixation structure 105 may provide an area to insert a tool that aids in removal. In alternative embodiments, fixation structure 105 may wrap completely around spermatic cord 14.

In the illustrated example, a gap 109 exists between spermatic cord 14 and fixation structure 105. Gap 109 may be filled with tissue or fluids and may provide a buffer that prevents microstimulator 106 from damaging spermatic cord 14. Alternatively, fixation structure 105 may be sized to wrap around spermatic cord 14 such that there is no gap between fixation structure 105 and spermatic cord 14.

Figure 12:
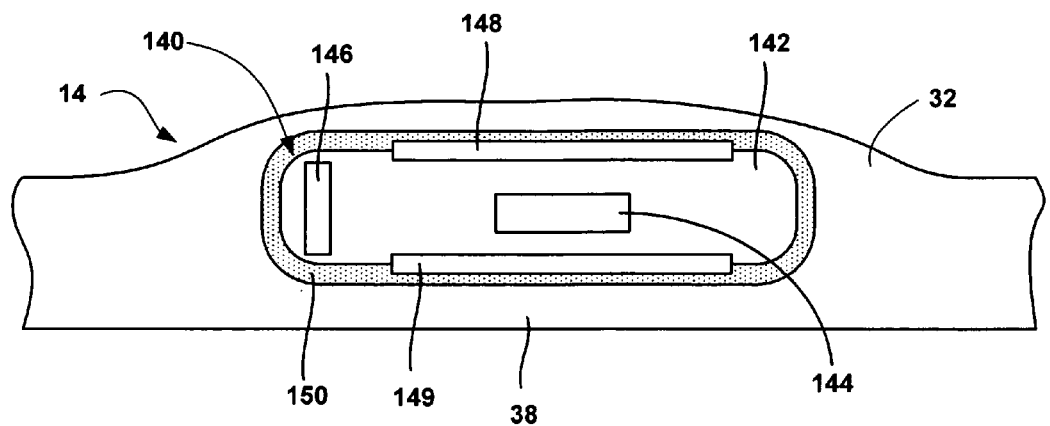
FIG. 12 is a side cross-sectional view of a leadless electrical microstimulator implanted within the spermatic cord.

FIG. 12 is cross-sectional view of a microstimulator 140 implanted within, for example, spermatic cord 14. Housing 142 of microstimulator 140 is embedded in the external fascia 32 of spermatic cord 14 and includes circuit board 144, power source 146, and electrodes 148 and 149. Housing 142 is in the shape of a rounded capsule and includes a smooth surface. The only structure extending from housing 142 are electrodes 148 and 149. Electrodes 148 and 149 may protrude slightly from housing 142 or, alternatively, may be integrated into housing 142 to apply electrical stimulation to external fascia 32. Microstimulator 140 rests in wall cavity 150 formed within external fascia 32. As previously described, microstimulator 140 may have a cylindrical shape with a diameter of less than or equal to approximately 2 cm and a length of less than or equal to approximately 5 cm.

Circuit board 144, power source 146, and electrodes 148 and 149 may be similar to respective circuit board 130, power source 132, and electrodes 108 of FIGS. 11A-C. Differences between these components of each embodiment may relate to the size or shape of each component. Therefore, electrodes 148 and 149 apply electrical stimulation under control of circuit board 144. Power source supplies operating power to circuit board 144. Circuit board 144 may select may select stimulation parameters and cause electrodes 148 and 149 to apply electrical pulses with the selected parameters according to schedules stored in memory. Circuit board 140 receives control signals from IMD 108, external programmer 109, or both by wireless telemetry. In some embodiments, one of electrodes 148 and 148 may comprise a sensor or microstimulator 140 may additionally include a sensor that detects a physiological parameter. In such embodiments, the sensor may sense a change in a physiological parameter. Processing electronics on circuit board 144 detects the change and causes electrodes to apply electrical stimulation in response to the change.

Implanting microstimulator 140 within external fascia 32 of spermatic cord 14 may be a simple method for securing electrodes 148 and 149. Microstimulator 140 may also be implanted in tissue proximate to genital nerve branch 22 or implanted in tissue proximate to genitofemoral nerve 20. In some embodiments, a plurality of microstimulators similar to microstimulator 140 may be implanted and apply electrical stimulation to spermatic cord 14 in a coordinated manner or in a manner independent of each other.

Figure 13:
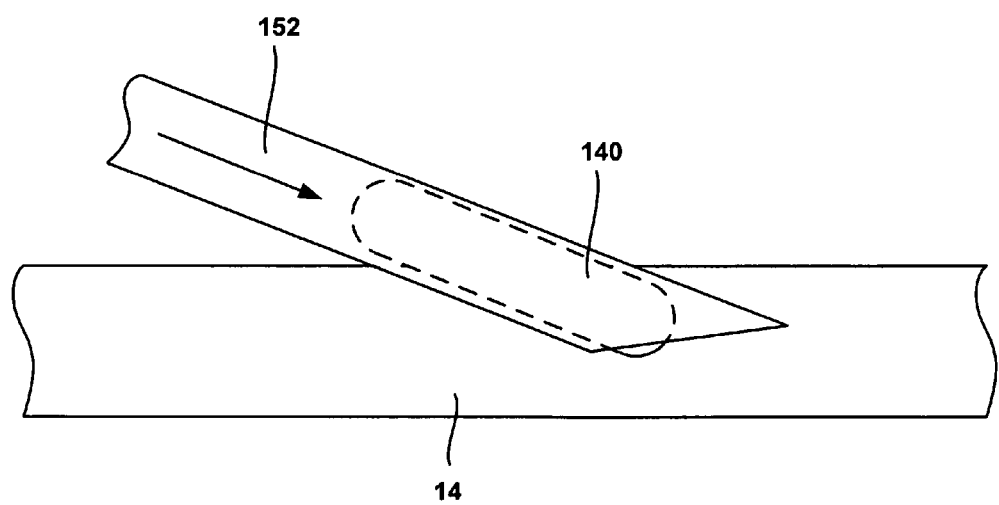
FIG. 13 is a schematic diagram illustrating implantation of a leadless microstimulator within the spermatic cord or tissue adjacent the spermatic cord.

FIG. 13 is a schematic diagram illustrating implantation of microstimulator 140 within the spermatic cord 14. Microstimulator 140 may be implanted through endoscopic, laparoscopic, or similar minimally invasive techniques. A surgeon may make a small inguinal incision in patient 10 and guides microstimulator 140 within needle 152 to spermatic cord 14. Needle 152 may be constructed of a metal alloy and comprise a hollow cylinder and a pointed distal end for puncturing the skin of patient 10. Needle 152 includes microstimulator 140 and a fluid or push rod to force microstimulator 140 out of the needle. An exemplary fluid may be saline or other biocompatible fluid.

Once needle 152 in positioned at the appropriate location with respect to spermatic cord 14, the surgeon may force microstimulator 140 into place. Removing needle 152 from spermatic cord 14 allows the external fascia of spermatic cord 14 to close and surround microstimulator 140. When implanting microstimulator 140, the external fascia should not be breached in order to prevent other structures within spermatic cord 14, such as the genital nerve branch, ductus deferens, lymph vessels, pampiniform plexus of veins which become the testicular vein, and testicular artery, from being damaged.

In other embodiments, microstimulator 140 may be implanted through more invasive procedures which expose spermatic cord 14. As previously described, multiple microstimulators may be implanted with spermatic cord 14 to apply electrical stimulation to a larger area. Microstimulator 140 may also be implanted within tissue proximate to the genital branch of the genitofemoral nerve.

Figure 14:
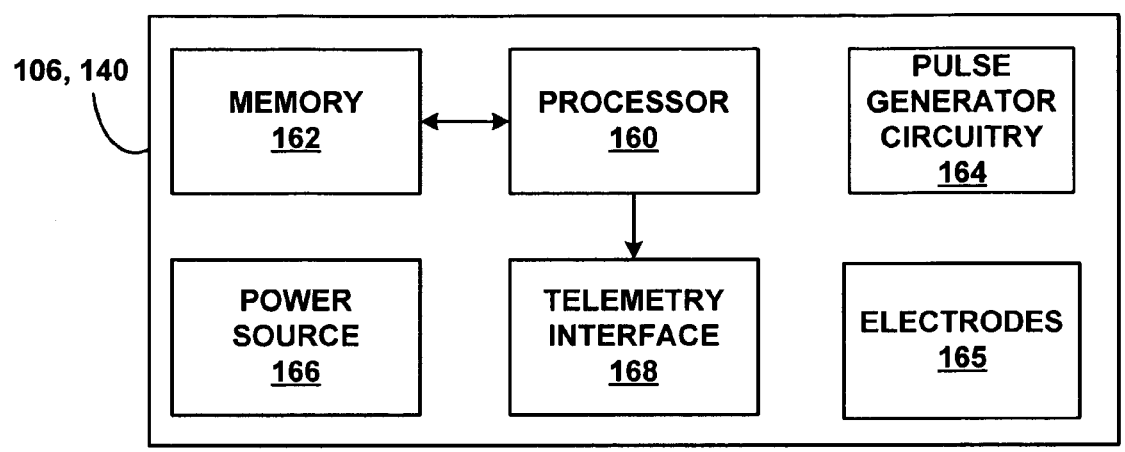
FIG. 14 is a functional block diagram illustrating various components of the leadless microstimulator of FIG. 12.

FIG. 14 is a functional block diagram illustrating various components of an example microstimulator 106 (FIG. 7) or microstimulator 140 (FIG. 12). In the example of FIG. 14, microstimulator 140 includes a processor 160, memory 162, pulse generator circuitry 164, telemetry interface 168, power source 166 and electrodes 165. Pulse generator circuitry 164 may be carried on a circuit board, along with processor 160, memory 162, and telemetry interface 168. Memory 162 may store instructions for execution by processor 160, stimulation parameters, e.g., electrode polarity, pulse width, pulse rate, and amplitude, and schedules for delivering electrical stimulation. Memory 162 may include separate memories for storing instructions, stimulation parameter sets, and schedules. Memory 162 may comprise any form of computer-readable media such as magnetic or optical tape or disks, solid state volatile or non-volatile memory, including random access memory (RAM), read only memory (ROM), electronically programmable memory (EPROM or EEPROM), or flash memory.

Processor 160 controls pulse generator circuitry 164 to deliver electrical stimulation via electrodes 165. Electrodes 165 may comprise any number and type of electrodes previously described, i.e., electrodes 108 (FIG. 7) and electrodes 148 and 149 (FIG. 12). An exemplary range of stimulation pulse parameters likely to be effective in treating, post vasectomy pain, genitofemoral neuralgia, and other conditions that cause long term pain in the testicles, groin, or abdomen when applied to the spermatic cord or genital nerve branch are as follows: pulse widths between approximately 10 and 5000 microseconds, more preferably between approximately 100 and 1000 microseconds and still more preferably between 180 and 450 microseconds; voltage amplitudes between approximately 0.1 and 50 volts, more preferably between approximately 0.5 and 20 volts and still more preferably between approximately 1 and 10 volts; and frequencies between approximately 0.5 and 500 hertz, more preferably between approximately 10 and 250 hertz and still more preferably between approximately 50 and 150 hertz. The pulses may be alternating current (ac) pulses or direct current (dc) pulses, and may be mono-phasic, bi-phasic, or multi-phasic in various embodiments. In addition, multiple patterns of pulses may be interleaved with one another to delivery different stimulation programs to the patient on a substantially concurrent basis.

Processor 160 also controls telemetry interface 168 to receive information from IMD 108, external programmer 109, or both. Telemetry interface 168 may communicate via wireless telemetry, e.g., RF communication, on a continuous basis, at periodic intervals, or upon request from the implantable stimulator or programmer. Processor 160 may include a single or multiple processors that are realized by microprocessors, Application-Specific Integrated Circuits (ASIC), Field-Programmable Gate Arrays (FPGA), or other equivalent integrated or discrete logic circuitry.

Power source 166 delivers operating power to the components of the implantable microstimulator. As mentioned previously, power source 166 may include a small rechargeable or non-rechargeable battery and a power generation circuit to produce the operating power.

Figure 15:
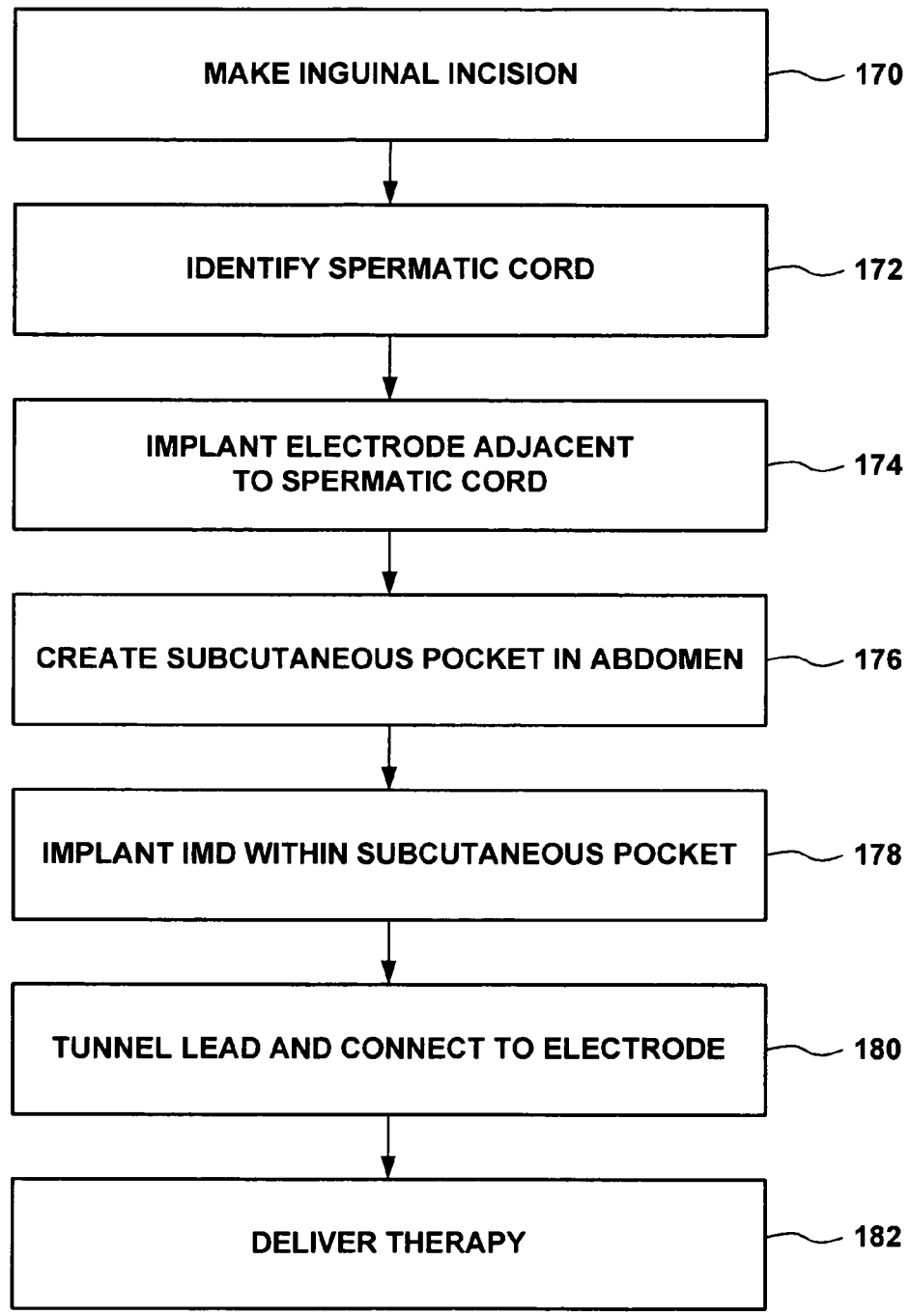
FIG. 15 is a flow chart illustrating a technique for applying electrical stimulation to a spermatic cord of a patient for alleviation of pelvic pain.

FIG. 15 is a flow chart illustrating a technique for applying electrical stimulation to a spermatic cord of a patient using an implantable electrode. Any of the previously described electrodes, i.e., cuff electrodes 16 and 17 (FIG. 1), electrodes 104 carried by lead 102 (FIG. 7), microstimulator 106 (FIG. 7), and microstimulator 140 (FIG. 12), may be implanted in accordance with the steps of the illustrated flow chart. The flow of events begins with the surgical procedure for implanting the electrode. The surgical procedure for exposing the spermatic cord for lead placement is well defined and may be used. Specifically, the surgeon makes an inguinal incision (170) as used for standard spermatic denervation or hernia repair.

The surgeon identifies the spermatic cord (172) and implants an electrode adjacent to the spermatic cord (174). When implanting a cuff electrode, the surgeon may elevate the spermatic cord using a primrose ring and wrap the cuff electrode around the spermatic cord. If the fixation structure of the spermatic cord is formed from a shape memory alloy, the body temperature of the patient may cause the fixation structure to recover its initial shape, i.e., a substantially closed cylinder or ring shape sized to fit around the spermatic cord. In any case, the cuff electrode may wrap at least partially around the spermatic cord thereby securing the cuff electrode to the spermatic cord.

When implanting lead 102 carrying electrodes 104, fixation elements such as hooks, barbs, helical structures, tissue ingrowth mechanisms, or other anchoring mechanisms may secure lead 102 to the spermatic cord or tissue proximate to the spermatic cord. Leads carrying electrodes may provide distinct advantages due to the number of electrodes available to apply electrical stimulation. For example, leads are available that carry eight, sixteen, or more electrodes which can be used to apply electrical stimulation in various groups or independently of each other. Further, because the electrodes may be positioned along a substantial length of the lead, the electrodes may apply electrical stimulation along a larger area of the spermatic cord.

The surgeon may implant microstimulator 106 similar to cuff electrodes 16 and 17 because the fixation structure of microstimulator 106 may operate in the same manner as the fixation structure of cuff electrodes 16 and 17. In contrast, the surgeon may implant microstimulator 140 within the external fascia of the spermatic cord using a needle. The needle may comprise a hollow cylinder and a pointed distal end for puncturing the skin of the patient and a fluid to force microstimulator 140 out of the needle. Accordingly, the surgeon may not need to make an inguinal incision when implanting microstimulator 140 within the external fascia of the spermatic cord. Rather, once the needle is positioned at the appropriate location with respect to the spermatic cord, the surgeon forces microstimulator 140 into place by depressing the plunger of the needle thereby forcing the fluid and microstimulator out of the needle.

Removing the needle from the spermatic cord allows the external fascia of the spermatic cord to close and surround microstimulator 140. Consequently, microstimulator 140 may be implanted with a minimally invasive surgical procedure. Additionally, in some embodiments, the surgeon may implant a plurality of microstimulators along the spermatic cord. The microstimulators may provide electrical stimulation independently or on a coordinated basis.

Although the implantation techniques have been described with respect to the spermatic cord, the implantation techniques may also be used to implant electrodes adjacent to the genital branch of the genitofemoral nerve. In particular, the surgeon may implant the electrode adjacent to the genital nerve branch before it joins the spermatic cord. Implanting an electrode adjacent to the genital nerve branch in this manner may provide paresthesia to a larger area of the patient because electrical stimulation is applied upstream of the spermatic cord.

In any case, after implanting the electrode, the surgeon may create a subcutaneous pocket in the abdomen of the patient (176) and implant an IMD, such as IMD 28 (FIG. 1) or IMD 108 (FIG. 7), within the subcutaneous pocket (178). In some embodiments, the IMD may be miniaturized and implanted within the scrotum of the patient. The surgeon may then tunnel the electrode lead through the patient to the implantation site and connect the lead to the implanted electrode(s) (180). Notably, microstimulators 106 and 140 may wirelessly communicate with external programmer 109 to receive control signals and, thus, not require an IMD.

When the surgical implantation procedure is complete, the implanted electrodes may apply electrical stimulation to deliver therapy (182) the spermatic cord or, alternatively, the genital nerve branch. Applying electrical stimulation to the spermatic cord may block pain signals from the testicles and the associated scrotal area from reach the central nervous system. The pain experienced by the patient may be unilateral or bi-lateral. Consequently, electrodes may be implanted adjacent to one or both spermatic cords of a patient. The pain experienced by the patient may also be constant or intermittent, or spontaneous or exacerbated by physical activities and pressure. Thus, the implanted electrodes may apply electrical stimulation on demand, such as in response to a control signal received from a patient or clinician programmer, or in accordance with preprogrammed cycles or schedules.

Electrical stimulation of the genitofemoral nerve or the genital nerve branch may provide may provide substantial relief of pelvic pain experienced by male and female patients, including urogenital pain or other forms of pelvic pain. In male patients, for example, electrical stimulation of the genitofemoral nerve or the genital nerve branch (directly or via the spermatic cord) may relieve a variety of pelvic pain conditions such as chronic testicular pain (CTP), post vasectomy pain, genitofemoral neuralgia, and other conditions that cause long term (chronic) pain in the testicles, groin, or abdomen. For female patients, electrical stimulation of the genitofemoral nerve or the genital nerve branch may alleviate a variety of pelvic pain conditions such as pain resulting from surgical procedures, vulvodynia, interstitial cystitis (painful bladder syndrome), adhesions, endometriosis, and pelvic congestion. Accordingly, although the invention has been primarily described with respect to male patients, the invention is not so limited and may be readily applied to female patients for similar relief of pain symptoms.

Many embodiments of the invention have been described. Various modifications may be made without departing from the scope of the claims. These and other embodiments are within the scope of the following claims.

The invention claimed is:

1. A method comprising applying electrical stimulation to a genital nerve branch of a genitofemoral nerve of a patient via an implanted electrical stimulation device, wherein the electrical stimulation is selected to alleviate pelvic pain, and wherein applying the electrical stimulation to the genital nerve branch comprises positioning an electrode proximate to the genital nerve branch at a point after the genitofemoral nerve has branched to form the genital nerve branch and a femoral nerve branch and applying the electrical stimulation via the electrode.

2. The method of claim 1, wherein the patient is a male patient, the method further comprising applying the electrical stimulation to the genital nerve branch via a spermatic cord of the patient.

3. The method of claim 1, wherein the patient is a male patient, the method further comprising applying the electrical stimulation to the genital nerve branch at a point on a side of an inguinal canal of the patient opposite a spermatic cord of the patient.

4. The method of claim 1, wherein the patient is a male patient, the method further comprising applying the electrical stimulation to the genital nerve branch at a point on a side of an inguinal canal of the patient adjacent a spermatic cord of the patient.

5. The method of claim 1, wherein the genital nerve branch of the genitofemoral nerve comprises a first genital nerve branch, and wherein the method further comprises applying electrical stimulation to a second genital nerve branch of a second genitofemoral nerve of the patient, wherein applying the electrical stimulation to the second genital nerve branch comprises positioning a second electrode proximate to the second genital nerve branch at a point after the second genitofemoral nerve has branched to form the second genital nerve branch and a second femoral nerve branch and applying the electrical stimulation via the second electrode.

6. The method of claim 5, wherein the patient is a male patient, the method further comprising applying the electrical stimulation to the first and second genital nerve branches via first and second spermatic cords of the patient.

7. The method of claim 5, wherein the patient is a male patient, the method further comprising applying the electrical stimulation to the first and second genital nerve branches at points on a side of respective inguinal canals of the patient opposite respective spermatic cords of the patient.

8. The method of claim 5, wherein the patient is a male patient, the method further comprising applying the electrical stimulation to the first and second genital nerve branches at points on a side of respective inguinal canals of the patient adjacent respective spermatic cords of the patient.

9. The method of claim 1, wherein the pelvic pain includes at least one of chronic testicular pain, post vasectomy pain, genitofemoral neuralgia, vulvodynia, and interstitial cystitis.

10. The method of claim 1, wherein the patient is a male patient, and wherein the electrical stimulation device comprises an electrode configured to at least partially engage a portion of the spermatic cord.

11. The method of claim 10, wherein the electrode includes at least one of a cuff electrode, a ring electrode, a planar electrode or an electrode on a leadless stimulator.

12. The method of claim 10, wherein the electrode includes a cuff electrode including a cuff-like fixation structure and one or more electrodes.

13. The method of claim 12, wherein the cuff electrode is mounted on an implantable medical lead coupled to the implantable electrical stimulation device.

14. The method of claim 12, wherein the implantable electrical stimulation device includes a leadless stimulator, and the cuff electrode is mounted on the leadless stimulator.

15. The method of claim 14, wherein the patient is a male patient, and wherein the fixation structure is flexible and at least partially conformable to the spermatic cord.

16. The method of claim 1, wherein the implantable electrical stimulation device includes a leadless stimulator sized for at least partial implantation within a facia of a spermatic cord of the patient.

17. A method comprising:
applying electrical stimulation, which is selected to alleviate pelvic pain, to at least a portion of a first genitofemoral nerve of a patient via an implanted electrical stimulation device at a point prior to the first genitofemoral nerve entering a first inguinal canal of the patient; and
applying electrical stimulation, which is selected to alleviate pelvic pain, to at least a portion of a second genitofemoral nerve of the patient at a point after the second genitofemoral nerve exits a second inguinal canal of the patient.

18. The method of claim 17, wherein the patient is a male patient, and wherein applying electrical stimulation to at least the portion of the first genitofemoral nerve comprises applying electrical stimulation to a genital nerve branch of the first genitofemoral nerve on a side of the first inguinal canal of the patient that is opposite a first spermatic cord of the patient.

19. The method of claim 17, wherein the patient is a male patient, and wherein applying electrical stimulation to at least the portion of the second genitofemoral nerve comprises applying electrical stimulation to a genital nerve branch of the second genitofemoral nerve on a side of the second inguinal canal of the patient that is adjacent a second spermatic cord of the patient.

20. The method of claim 17, wherein the pelvic pain includes at least one of chronic testicular pain, post vasectomy pain, genitofemoral neuralgia, vulvodynia, and interstitial cystitis.

21. The method of claim 17, wherein the patient is a male patient, and wherein the implanted electrical stimulation device comprises an electrode configured to at least partially engage a portion of a spermatic cord of the patient.

22. The method of claim 21, wherein the electrode includes at least one of a cuff electrode, a ring electrode, a planar electrode or an electrode on a leadless stimulator.

23. The method of claim 21, wherein the electrode includes a cuff electrode including a cuff-like fixation structure and one or more electrodes.

24. The method of claim 23, wherein the cuff electrode is mounted on an implanted medical lead coupled to the implanted electrical stimulation device.

25. The method of claim 23, wherein the implanted electrical stimulation device includes a leadless stimulator, and wherein the cuff electrode is mounted on the leadless stimulator.

26. The method of claim 25, and wherein the cuff-like fixation structure is flexible and at least partially conformable to the spermatic cord.

* * * * *